United States Patent
Abumoussa et al.

(10) Patent No.: US 11,640,682 B2
(45) Date of Patent: May 2, 2023

(54) METHODS, SYSTEMS, AND COMPUTER READABLE MEDIA FOR PROCESSING DIGITAL SUBTRACTION ANGIOGRAPHY (DSA) AND COMPUTED TOMOGRAPHY (CT) IMAGES FOR REDUCING RADIATION EXPOSURE IN DSA AND CT SUBJECTS

(71) Applicant: The University of North Carolina at Chapel Hill, Chapel Hill, NC (US)

(72) Inventors: Andrew Lateef Abumoussa, Durham, NC (US); Yueh Zenas Lee, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 394 days.

(21) Appl. No.: 17/040,037

(22) PCT Filed: Mar. 22, 2019

(86) PCT No.: PCT/US2019/023697
§ 371 (c)(1),
(2) Date: Sep. 21, 2020

(87) PCT Pub. No.: WO2019/183555
PCT Pub. Date: Sep. 26, 2019

(65) Prior Publication Data
US 2021/0027502 A1 Jan. 28, 2021

Related U.S. Application Data

(60) Provisional application No. 62/646,831, filed on Mar. 22, 2018.

(51) Int. Cl.
*G06T 11/00* (2006.01)
*A61B 6/03* (2006.01)
*A61B 6/00* (2006.01)

(52) U.S. Cl.
CPC ............ *G06T 11/008* (2013.01); *A61B 6/032* (2013.01); *A61B 6/481* (2013.01); *A61B 6/504* (2013.01);
(Continued)

(58) Field of Classification Search
CPC ................. G06T 11/008; G06T 11/006; G06T 2211/404; G06T 2207/10016;
(Continued)

(56) References Cited

U.S. PATENT DOCUMENTS 5,150,292 A * 9/1992 Hoffmann .............. A61B 6/507
600/431
6,490,337 B1 12/2002 Nagaoka et al.
(Continued)

FOREIGN PATENT DOCUMENTS

EP 0 869 738 B1 2/2004
WO WO 2017/112554 A1 6/2017

OTHER PUBLICATIONS

Notification of Transmittal of the International Search Report and the Written Opinion of the International Searching Authority, or the Declaration for International Application No. PCT/US2019/023697 (dated Jul. 4, 2019).
(Continued)

*Primary Examiner* — Courtney D Thomas
(74) *Attorney, Agent, or Firm* — Jenkins, Wilson, Taylor & Hunt, P.A.

(57) ABSTRACT

A method for processing digital subtraction angiography (DSA) or computed tomography (CT) images for reduced radiation exposure to a DSA or CT subject includes receiving, as input, a plurality of captured DSA or CT image frames of a contrast agent flowing through a volume of interest in a subject. The method further includes fitting a mathematical model to measured contrast agent density of
(Continued)

individual voxels of the captured DSA or CT image frames to produce a mathematical model of contrast agent flow across the captured DSA or CT image frames. The method further includes sampling the mathematical model of contrast agent flow for the individual voxels to produce reconstructed DSA or CT image frames. The method further includes outputting at least one of the reconstructed CT or DSA image frames.

19 Claims, 16 Drawing Sheets

(52) U.S. Cl.
CPC ............ *A61B 6/507* (2013.01); *A61B 6/5205* (2013.01); *G06T 11/006* (2013.01); *G06T 2211/404* (2013.01)

(58) Field of Classification Search
CPC . G06T 2207/10076; G06T 2207/10081; G06T 2207/10116; G06T 2207/30104; G06T 7/0016; A61B 6/032; A61B 6/481; A61B 6/504; A61B 6/507; A61B 6/5205; A61B 6/487
See application file for complete search history.

(56) References Cited

U.S. PATENT DOCUMENTS

| | | |
|---|---|---|
| 6,546,275 B2 | 4/2003 | Carroll |
| 2004/0077941 A1 | 4/2004 | Reddy et al. |
| 2008/0097197 A1 | 4/2008 | Kalafut et al. |
| 2011/0037761 A1 | 2/2011 | Mistretta et al. |
| 2011/0206259 A1 | 8/2011 | Mistretta et al. |
| 2012/0114217 A1 | 5/2012 | Mistretta et al. |
| 2012/0323118 A1 | 12/2012 | Menon Gopalakrishna et al. |
| 2014/0270053 A1 | 9/2014 | Larson |
| 2017/0172450 A1 | 6/2017 | Koay et al. |

OTHER PUBLICATIONS

Austein et al., "Comparison of Perfusion CT Software to Predict the Final Infarct Volume After Thrombectomy," Stroke, pp. 2311-2317 (Sep. 2016).
Niu et al., "Low-dose cerebral perfusion computed tomography image restoration via low-rank and total variation regularizations," Neurocomputing, vol. 197, pp. 1-38 (Jul. 12, 2016).
Lin et al., "Whole-Brain CT Perfusion to Quantify Acute Ischemic Penumbra and Core," Radiology, vol. 279, No. 3, pp. 876-887 (Jun. 2016).
Racadio et al., "Significant Dose Reduction for Pediatric Digital Subtraction Angiography Without Impairing Image Quality: Preclinical Study in a Piglet Model," American Journal of Radiology, vol. 203, pp. 904-908 (Oct. 2014).
McGehee et al., "Brain Perfusion Imaging: How Does it Work and What Should I Use?" Journal of Magnetic Resonance Imaging, vol. 36, pp. 1257-1272 (2012).
Patil et al., "An improved model for describing the contrast bolus in perfusion MRI," Med. Phys., vol. 38, No. 12, pp. 6380-6383 (Dec. 2011).
Krissak et al., "Noise Reduction and Image Quality Improvement of Low Dose and Ultra Low Dose Brain Perfusion CT by HYPR-LR Processing," PLoS One, vol. 6, No. 2, pp. 1-8 (Feb. 2011).
Bredno et al., "Simulation Model for Contrast Agent Dynamics in Brain Perfusion Scans," Magnetic Resonance in Medicine, vol. 64, pp. 280-290 (2010).
Paldino et al., "Fundamentals of Quantitative Dynamic Contrast-Enhanced MR Imaging," Magn Resn Imaging Clin N Am, vol. 17, pp. 1-13 (2009).
Brenner et al., "Computed Tomography—An Increasing Source of Radiation Exposure," The New England Journal of Medicine, vol. 357, No. 22, pp. 1-8 (Nov. 29, 2007).
Hirata et al., "A Method for Reducing Radiation Dose in Cerebral CT Perfusion Study with Variable Scan Schedule," Radiation Medicine, vol. 23, No. 3, pp. 162-169 (2005).
Chan et al., "Simplified Gamma-Variate Fitting of Perfusion Curves," IEEE, pp. 1067-1070 (2004).
Jackson, "Analysis of dynamic contrast enhanced MRI," The British Journal of Radiology, vol. 77, pp. S154-S166 (2004).
Eastwood et al., "Perfusion CT with Iodinated Contrast Material," AJR, vol. 180, pp. 3-12 (Jan. 2003).
Li et al., "Erroneous and inappropriate use of gamma fits to tracer-dilution curves in magnetic resonance imaging and nuclear medicine," Magnetic Resonance Imaging, vol. 21, pp. 1-2 (2003).
Koenig et al., "Perfusion CT of the Brain: Diagnostic Approach for Early Detection of Ischemic Stroke," Radiology, vol. 209, pp. 1-10 (1998).
Benner et al., "Accuracy of Gamma-Variate Fits to Concentration-Time Curves from Dynamic Susceptibility-Contrast Enhanced MRI: Influence of Time Resolution, Maximal Signal Drop and Signal-to-Noise," Magnetic Resonance Imaging, vol. 15, No. 3, pp. 307-317 (1997).
Madsen, "A simplified formulation of the gamma variate function," Phys. Med. Biol., vol. 37, pp. 1-5 (1992).
Rosen et al., "Contrast Agents and Cerebral Hemodynamics," Magnetic Resonance in Medicine, vol. 19, pp. 285-292 (1991).
Belliveau et al., "Functional Cerebral Imaging by Susceptibility-Contrast NMR," Magnetic Resonance in Medicine, vol. 14, pp. 538-546 (1990).
Rosen et al., "Perfusion Imaging with NMR Contrast Agents," Magnetic Resonance in Medicine, vol. 14, pp. 249-265 (1990).

* cited by examiner

METHODS, SYSTEMS, AND COMPUTER READABLE MEDIA FOR PROCESSING DIGITAL SUBTRACTION ANGIOGRAPHY (DSA) AND COMPUTED TOMOGRAPHY (CT) IMAGES FOR REDUCING RADIATION EXPOSURE IN DSA AND CT SUBJECTS

PRIORITY CLAIM

This application claims the priority benefit of U.S. Provisional Patent Application Ser. No. 62/646,831, filed Mar. 22, 2018, the disclosure of which is incorporated herein by reference in its entirety.

TECHNICAL FIELD

The subject matter described herein processing DSA and CT images. More particularly, the subject matter described herein relates to processing DSA and CT images to reduce radiation exposure in DSA and CT subjects.

BACKGROUND

DSA involves obtaining an initial x-ray image of tissue in a subject without contrast agent followed by a series of x-ray images of contrast agent flowing through the tissue in the subject. For example, one DSA protocol may involve obtaining 3 frames of x-ray images per second for 10 seconds. During each image acquisition frame, the subject is exposed to radiation. It is desirable to limit the amount of radiation exposure to the subject in DSA image acquisition.

CT image acquisition, like DSA image acquisition, involves exposing the subject to radiation. Thus, in performing CT image acquisition, it is also desirable to reduce radiation exposure of the subject.

Mathematical models have been used to model the flow of contrast agent through tissue. However, such mathematical models have either been applied after the fact to determine how a model would perform in the presence of noise or are too computationally expensive to be practical for real-time clinical use. Accordingly, in light of these difficulties, there exists a need for improved methods, systems, and computer readable media for processing DSA and CT images to reduce radiation exposure to DSA and CT subjects.

SUMMARY

A method for processing digital subtraction angiography (DSA) or computed tomography (CT) images for reduced radiation exposure to a DSA or CT subject includes receiving, as input, a plurality of captured DSA or CT image frames of a contrast agent flowing through a volume of interest in a subject. The method further includes fitting a mathematical model to measured contrast agent density of individual voxels of the captured DSA or CT image frames to produce a mathematical model of contrast agent flow across the captured DSA or CT image frames. The method further includes sampling the mathematical model of contrast agent flow for the individual voxels to produce reconstructed DSA or CT image frames at a clinician's desired frame-rate. The method further includes outputting at least one of the reconstructed CT or DSA image frames.

A system for processing digital subtraction angiography (DSA) or computed tomography (CT) images for reduced radiation exposure to a DSA or CT subject includes a computing platform including at least one processor. The system further includes a model fitter executable by the computing platform using the at least one processor for receiving, as input, a plurality of captured DSA or CT image frames of a contrast agent flowing through a volume of interest in a subject and fitting a mathematical model to measured contrast agent density of individual voxels of the captured DSA or CT image frames to produce a mathematical model of contrast agent flow across the captured DSA or CT image frames. The system further includes an image reconstructor executable by the computing platform using the at least one processor for sampling the mathematical model of contrast agent flow for the individual voxels to produce reconstructed DSA or CT image frames and outputting at least one of the reconstructed CT or DSA image frames.

The subject matter described herein for processing DSA and CT images to reducing radiation exposure in DSA or CT subjects may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

DETAILED DESCRIPTION

Figure 1:
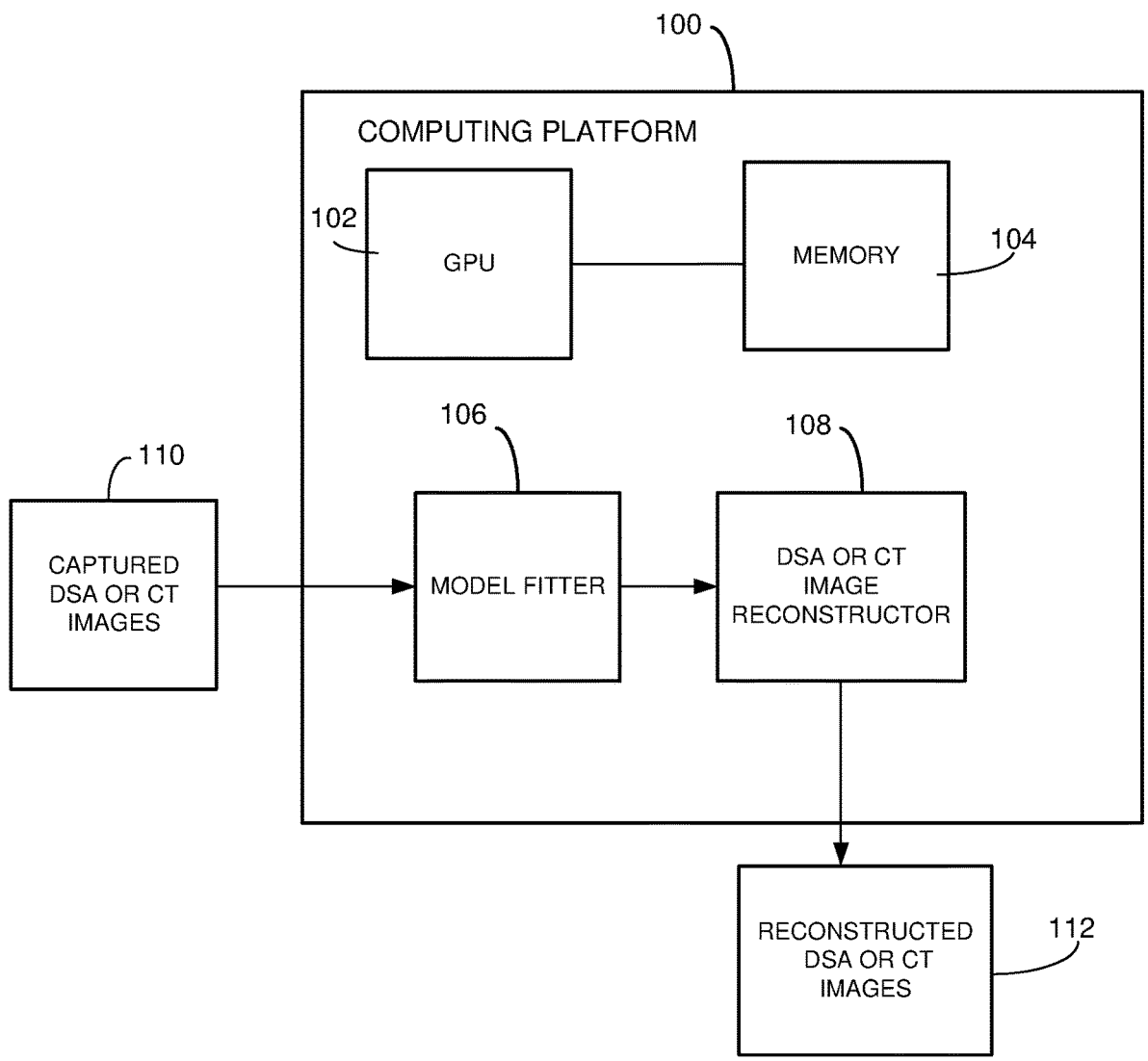
FIG. 1 is a block diagram of a system for processing DSA or CT images to reduce radiation exposure in DSA or CT subjects.

DSA offers high quality, spatially and temporally resolute imaging of the vasculature and is often essential in vascular, cardiac, neurovascular and other interventional evaluations and surgical planning. Despite its clinical utility, DSA exposes patients to some of the highest cumulative doses of radiation as compared to other imaging modalities. Given the increased potential for deterministic and stochastic effects with higher radiation dosages, there is a definite need to reduce radiation doses associated with DSA imaging. We sought to develop a processing framework to reduce radiation dosages by reconstructing DSA studies from low frame rate acquisitions. Our approach leverages flow modeling techniques of blood and contrast through an organ's parenchyma to reduce the number of image acquisitions required to complete these studies.

The subject matter described herein demonstrates the feasibility of a DSA frame reconstruction processing method which leverages flow modeling techniques to reduce the number of image acquisitions and thus radiation dose required in DSA.

Methods: In our work described herein, 50 consecutive digital subtraction angiography (DSA) studies were analyzed and processed. Perfusion analysis of the original study was performed for 5 different pathologies during post-processing retrospectively. Experiments were conducted by simulating image capture at a reduced frame rate. These simulated images were then used to fit a model to the contrast response curve, reconstruct images to match the original frame rate, and then used to measure perfusion (2D-PA). Our software automatically determines the arterial input function (AIF) and the venous output function (VOF) at every voxel to provide exact measurements of the arrival time (AT), time to peak (TTP), mean-transit-time (MTT), blood flow and volume (BF/BV) for perfusion mapping. After study reconstruction, cumulative errors for HU, AT, TTP, MTT, and BF/BV were recorded for each simulated frame rate as compared to original study.

Results: This work demonstrates that clinicians can reduce radiation exposure for digital subtraction angiography by increasing intervals between acquisitions. We have determined that we can reduce the frame acquisition for DSAs by a factor of 4 with minimal loss in image quality at reconstruction and CT perfusions by a factor of 10.

Conclusion: 2D-PA parameters allow for an accurate and objective quantification of error when assessing the quality of dose reduction techniques for DSA. We have found that frame rates of DSA can be effectively reduced to 75% of the original dose with no loss of image fidelity.

INTRODUCTION

Digital subtraction angiography (DSA) is a common imaging modality used in neurosurgical, neurological, and other interventional procedures. DSA imaging produces some of the highest cumulative radiation dosages among medical imaging modalities. It becomes imperative that clinicians tailor image acquisition protocols to minimize cumulative radiation exposure. Notably, current work has validated extending the time window for stroke interventions from 6 to 24 hours, which will inevitably further increase the utilization of these studies [1][2]. Image acquisition parameters, such as frame rate and radiation dose are set using a combination of predetermined protocols and automatic exposure controls often optimized to provide the best quality image. Diagnostic criteria for many pathologies as well as determining a patient's eligibility for certain vascular interventions requires DSA imaging. Often, interventionalists need to know the size, anatomy, and vascular characteristics of vessels as well as perfusion to accurately plan their procedures; high quality imaging is a necessity. There is limited information on the effect lower frame-rates have on imaging integrity. Patients undergoing these studies often require multiple scans during both the diagnostic or interventional procedures and are thus subjected to even larger cumulative doses of radiation; however cumulative effect of this radiation exposure has not been evaluated. Prior work has evaluated image quality and signal characteristics of brain perfusion CT obtained by low dose and ultra-low-dose protocols both with and without post processing demonstrating initial feasibility of this type of work [3].

Theory

We briefly review the definitions for key perfusion parameters: mean transit time (MTT), cerebral blood volume (CBV), and cerebral blood flow (CBF) in order to describe their interdependence with respect to the central volume theorem. These definitions lead to the central equation defining CBF when using non-diffusible tomographic tracers during perfusion analysis. Accurate modeling of perfusion parameters provides an objective measure of error during the evaluation of reconstructed angiographic studies. When a bolus of contrast is administered at time t=0 into a feeding vessel for a volume of interest (VOI) of tissue, the individual particles of the contrast material travel through different paths throughout the VOL. Their transit times have a distribution characteristic of both the flow and the underlying vascular structure. The probability density function of these transit times is traditionally denoted h(t) and called the transport function. Measurements of perfusion require knowledge of how much contrast is introduced into a volume, referred to as the arterial input function CA(t), and the concentration of tracer in the venous output is denoted CV (t). The relationship between the venous output and arterial input functions is defined as:

$$C_V(t) = C_A(t) \otimes h(t) \quad [\text{Eq 1}]$$

where $\otimes$ denotes a convolution. The fraction of injected tracer present in the vasculature at time t is described by the residue function R(t).

$$R(t) = 1 - \int_0^t h(\tau)d\tau \quad [\text{Eq 2}]$$

Note that the definition of h(t) as a probability density function leads to R(0)=1, and R(t)>0 and decreasing for all t. The amount of intravascular tracer that traverses through a VOI is determined by:

$$CBV_{VOI} = \frac{\int_{-\infty}^{\infty} C_{VOI}(\tau)d\tau}{\int_{-\infty}^{\infty} C_A(\tau)d\tau}$$

In the case of brain tissue with an intact blood brain barrier (BBB), the distribution space of common contrast agents is equal to the plasma volume (specifically, the intravascular, extracellular space). The fraction of tissue available for tracer distribution is (1-Hctm)*CBVf where Hctm is the microvascular hematocrit and CBVf is the cerebral full blood volume. Hctm is a complicated function of vessel size, flow and pathophysiological conditions but is generally 40-100% of the systemic blood hematocrit. The discussion of these effects is outside the scope of this paper. Throughout the rest of the discussion herein, the values of CBF and CBV will refer to full blood flow with a macrovascular to microvascular hematocrit ratio of ⅔, independent of flow, commonly accepted simplifications.

The central volume theorem states that the relationship between tissue flow (CBF), blood volume (CBV) and MTT is:

$$MTT = \frac{CBV}{CBF}$$

The concentration (t) of tracer within a VOI can then be rewritten:

$$C_{VOI}(t) = CBF(t) \int_0^t C_A(\tau) R(t - \tau) d\tau$$

This equation is the central equation in our approach to determine flow using non-diffusible tracers. It states that the initial height of the deconvolved concentration time curve equals the flow, CBF(t). It is important to note that the AIF in the last equation may undergo dispersion during its passage from the point of measurement to peripheral tissue. The dispersion can be described mathematically as a convolution with a vascular transport function h*(t). If the residue function determined using the AIF that is subsequently dispersed is denoted R*(t) and the "true" residue function R(t) would consequently yield R*(t)=h*(t) R(t). The initial height of the deconvolved curve thus underestimated by the spread of R*(t). This is the reason that the software we have created evaluates the perfusion over every voxel by identifying the appropriate AIF over a 5×5 voxel local search.

Deconvolution

Approaches to deconvolve these equations are discussed elsewhere [10]. Our software transforms the convolution to an algebraic problem. Unfortunately, we know that the concentrations are not constant between each measured time value, making this approach extremely sensitive to noise. In the context of cerebral imaging, the assumption of rCBF measurements using stand tomographic imaging of intravascular bolus passages, we know that the AIF and residue function are expected to vary over small scales relative to the temporal resolution of the imaging hardware. This makes the assumption of constancy across image acquisitions a poor approximation. In our approach we assumed that Ca(t) and R(t) both vary linearly with time.

Material & Methods

This retrospective study was approved by our institution's IRB committee. We enrolled 50 consecutive patients undergoing digital subtraction angiography for 5 neurological diseases between. No normal controls were used due to the invasive nature of DSA imaging. Initial diagnosis was confirmed during imaging. To quantify the utility of this software, no exclusion criteria were applied. The only inclusion criteria for this study was that each angiographic study included must have had a total 12 or more acquired images during a series. 12 acquisitions allowed a minimum of three images to be used during the mathematical modeling of rate reduced images during experimentation. Indication for the original image acquisition was determined by standard of care.

Data Acquisition

DSA examinations were performed by two experienced interventional neuroradiologists and one experienced endovascular neurosurgeon. Images were obtained using a biplane angiography suite (Artis Zeego, Siemens AG, Erlange, Germany). According to our standard protocol, the patients were placed in a supine position on the angiography table, both groins were prepped and draped in the usual sterile fashion, and vascular access was obtained using the Seldinger technique. A 5-French, 10-cm sheath (Pinnacle, Terumo) was placed in the right common femoral artery. Under fluoroscopic guidance, the vessels of interest were selectively catheterized using a 5-French angled taper catheter (Glidecath, Terumo, Tokyo, Japan) and digital subtraction angiography was performed with images of the intracranial circulation. Images were acquired at 2 frames per second, with a range of 10-30 s, and commencing simultaneously with contrast injection. Image data was anonymized and transferred offline for analysis. Initial frame rates for each study were set by the treating physician. 2D-Perfusion Analysis (2D-PA) was performed on DSA studies acquired with a catheter placed in the distal internal carotid artery for error analysis.

Perfusion Analysis

Perfusion analysis of DSA studies is not routinely performed, nor standardized at this time. However, to measure the accuracy and resilience of our DSA reconstruction method (process described below) from low frame rate acquisitions, perfusion analysis was performed on both, the original study and reconstructed images. The arterial input and venous output functions used for perfusion analysis parameters were automatically selected by our software using a local 5×5 voxel search at each voxel to identify the direction of contrast travel relative to each voxel of interest. This minimizes quantification errors during the perfusion calculation by minimizing the effects of contrast dispersion between frames. Standard singular value decomposition was used for the deconvolution algorithm to obtain TTP, CBV, CBF, and MTT. Numeric density values for AT, TTP, LT, MTT, peak density, area under the curve were recorded for each voxel of each study.

Statistical Analysis

Statistical analysis of the patient demographics and angiographic data were calculated and are presented as the mean +/−standard deviation in Table 1. Overall accuracy of the reconstructed images was assessed by measuring differences in key perfusion parameters and hounsfield units at each time point. Comparisons between the original study and reconstructed images were made using errors in HU, AT, TTP, MTT. In addition, differences between the measured and calculated perfusion statistics were compared using a chi-squared test. A p value of <0.05 was defined as significant.

Experimental Design

This work evaluated the level of radiation dose reduction possible for DSA through decreased sampling rates during image acquisition. To test how well contrast dosage models reproduce the shapes of tissue concentration curves, each study's frame-rate was experimentally reduced. The tissue concentration curves were then mathematically modeled using a subset of frames compromising ½, ⅓ and ¼ of the frames from the original study. Images were then reconstructed by sampling the resultant model fit to the subset of images to produce a study at the original frame rate. We present two experiments: the first examines the use of a 4th degree polynomial or gamma variates as possible models for the contrast density curves and then measured the errors of the perfusion data parameters AT, TTP, MTT and the quantitatively computed CBF and CBV maps. Secondly, we present a reader study to measure the clinical quality of the reconstructed studies.

Model Fitting: For each study, tissue concentration curves were modeled at each voxel using the "available" numbers of frames. Five sets of models were fit to each study using all of the acquired frames, every 2nd frame, every 3rd frame, every 4th frame and then every 5th frame, respectively. All possible offsets were evaluated to see if timing of the contrast agent administration affects the fit of the model. Goodness of fit at each voxel was statistically analyzed by measuring the residuals, RHU, between the hounsfield units calculated from sampling the model, HUm(t), and the original study, HUo(t), along with a comparison of the errors of the modeled perfusion statistics for each tissue co concentration curve.

$$R_{HU} = \sum_{0}^{n} [HU_o(t) - HU_m(t)]^2 / 2n$$

$$R_{AT} = (AT_o - AT_m)^2 / AT_o^2$$

$$R_{TTP} = (TTP_o - TTP_m)^2 / TTP_o^2$$

$$R_{TTP} = (MTT_o - MTT_m)^2 / MTT_o^2$$

[Gamma Variate]$S(t) = A\ t^\alpha e^{-\beta t}$ (1)

Mathematically, the values for A, α,β describe the gamma variate function of the form of equation (1). Our software performs this fitting at each voxel through a series of data transformations. The steps for this transformation are described as follows.

Step 1: Identify the arrival time (AT) defined to be the point where the concentration curve rises to a level of 10% of the overall range of concentrations for this study. If no single time point is found, then an estimated AT is determined by applying a linear fit, m(t), between the minimum and maximum concentration values for a given voxel and then identifying the time point, AT, where the value of the fit satisfies:

$m(AT) = m(t_{min}) + 1/10[m(t_{max}) - m(t_{min})]$.

Step 2: Identify the time to peak, $t_{max}$, defined to be the point where the dose response curve is at the maximum, max_val Step 3: Identify the leave time (LT), defined to be the point where the dose response curve stops decreasing after the maximum value. If no value is observed that satisfies this condition, then the LT is determined by applying a linear fit, m(t), between the maximum and minimum concentration value after the maximum for a given voxel and then identifying the time point, LT, where the value of the fit satisfies:

$m(LT) = m(t_{min}) + 1/10[m(t_{max}) - m(t_{min})]$

Step 4: We then solve for all the parameters of the gamma variate function A, a, b as follows.

$a$=slope of function defined by $x = 1 + \log[(t-AT+1)/(t_{max}-AT+1)] - (t-AT+1)/(t_{max}-AT+1)$ for $t$ belonging to $[AT, LT]$ $y = \log(HU_t - HU_{AT})$ $b = (t_{max} - AT)/a$ $A = (\max\_val)^* (t_{max} - AT)^* e^a$ Step 5: Logarithmic regression to find the recirculation bolus, defined f=a+b ln(t), where f=$HU_{actual}$-$HU_{GV}$ With the completed model then becoming S(t)=A t e−t+ a+b ln(t). This completed model allows us to sample this curve at any interval we desire to reconstruct the study.

Reconstructed image quality: After fitting the mathematical models to the tissue concentration curve from a subset of frames of the original angiography, reconstructed images are generated by sampling the continuous model at a desired frame-rate [11]. Reconstructed images are compared voxel by voxel to the original studies at each corresponding time point. Differences in voxel intensity, arrival time, time-to-peak, AUC, rMTT were measured for each study. Each study was reconstructed to achieve ½, ⅓, and ¼ frame rates respectively.

DSA Reconstruction

DSA reconstruction is performed after modeling the tissue concentration curve at each voxel with either a 4th degree polynomial or gamma-variate function. With the curve that best fits the "available" frames from a given study, reconstructed images are returned by sampling the model at the desired frame rate be returned by sampling the model. Previous work has demonstrated that fourth degree polynomials, gamma variate functions and modified gamma variate functions perform best [21]. Gamma variate fitting of tissue concentration curves have been previously evaluated with simulated experiments [11]-[13]. Our experiments examine the sole use of gamma variates or polynomial functions to model the complete contrast traversal through the tissue of interest. Ideally, the recirculation bolus would be modeled. Because the concentration curves are not purely gamma-variate distributions, we accept errors due to recirculation artifact [14]. For this work we, note the importance of modeling this for our future work. Each image is deconstructed to these basis representations of their time-signal curve S(t). Each voxel's time-signal curve can then be converted into concentration curves C(t) which is proportional to the contrast agent concentration according to [13]-[15], [15]-[17]

[Gamma Variate]$S(t) = A\ t^\alpha e^{-\beta t}$

[Concentration]$C(t) = -k \ln[S(t)/S_o]$

Where k is an unknown constant, S(t) is the signal intensity at time point t and So is the baseline DSA signal intensity before the administration of contrast tracer. Stirling's or Lanczos's formula: Previous work has discussed pitfalls of modeling tracer-dilution curves in medical applications. Citing coarse sampling rates of MRI imaging, the bias introduced into common gamma variate fittings often lead to an estimation of parameters with errors as great as 50% [18]. Stirling's and Lanczo's formulas that leverage a local density random walk distribution for Brownian motion with positive drift enables proper estimation of AT and MTT while taking into account back-dispersion, using very few points (as long as the coefficients in (3) are known to 15 decimal points).

$$C(t) = \sqrt{2\pi} * (B+5.5)^B * e^{-(B+5.5)} * \left[1 + \sum_{1}^{6} \frac{k_v}{B+i}\right]$$

9. Image Quality Analysis:

Subjective image quality of the reconstructed images and the corresponding DSA were assessed on a 5-point scale (1: excellent, 5: non-diagnostic) in consensus by two neuroradiologists blinded to the dataset acquisition/post-processing technique. Images were evaluated in a randomized, blinding, offline readings. The anonymized images were randomly displayed independently at full dose, half-dose, one-third dose, and one-quarter dose. Three experienced neuroradiologists graded images from the arterial, capillary and venous phases separately according to the criteria defined in Table 2. The diagnostic quality of images from each phase was evaluated on a scale of 1 to 5, as detailed below. Overall image quality was defined as the sum of scores from each independent neuroradiologist.

TABLE 2

| Score | Interpretation of DSA Acquisition |
| --- | --- |
| 0 (Nondiagnostic) | Failing to depict arterial structures in any meaningful way |
| 1 (Poor) | Enabling diagnostic evaluation of first-order branches relative to the injected vessel only |
| 2 (Intermediate) | Enabling diagnostic evaluation up to second-order branches relative to injected vessel |
| 3 (Good) | Enabling diagnostic evaluation up to third-order branches relative to injected vessel |
| 4 (Excellent) | Enabling diagnostic evaluation up to vessels beyond third-order branches relative to injected vessel |

Statistical Analysis

Pearson correlation coefficients were calculated to assess the correlations within every voxel between the attenuation values in the original and the post-processed datasets. Bland-Altman analysis was also applied to evaluate the agreement between the mean attenuation values of the above listed datasets [15]. Area under the attenuation curve (AUC), maximum attenuation, and minimum attenuation in the brain parenchyma were assessed in each time series. The signal to noise ratio (SNR) of the brain parenchyma in every time series was calculated as mean SNR of all images in the time series. Paired Student's t-test was calculated to compare the AUC, maximum attenuation, minimum attenuation and SNR values between the datasets.

Computing Equipment:

This software was written in Java as a multi-threaded algorithm capable of performing this analysis on both CPUs and GPUs. All computational times are reported as run on a 2013 Apple MacBook Air running on Mac OS High Sierra 10.13.2 with a 1.7 GHz Intel Core i7 processor and 8 GB 1600 MHz DDR3 Ram. Computational time and accuracy are reported as runs on the CPU as well as an external GPU due to Intel's integrated GPU lacking support for double precision math at the time of this report.

Results

Baseline Dose Study

Reconstructed AP DSA studies at 2×, 3× and 4× reductions demonstrated an average voxel error of −6.5%±1.5%, 2%±2.5% and 27%±2% respectively. Reconstructed lateral DSA studies at 2×, 3× and 4× reductions demonstrated an average voxel error of 2%±2.2%, 15%±3.1%, 14.75%±13% respectively.

Perfusion Parameters 2D-PA is not routinely performed on DSA images. For this work, we perform perfusion analysis on the original study and reconstructed images to provide another form of validation and error measure. Errors in AT for all the voxels were −0.01+/−0.110 seconds at both 50% and 33% dose reductions. TTP errors were 0.5+/−0.066 seconds at a 50% reduction and 1.48+/−0.71 seconds at a 33% reduction.

Subjective Image Quality: A reader study will be performed to validate the clinical utility of these reconstructed images to determine the diagnostic quality.

Discussion

One of the basic recommended standards for radiographic imaging by the International Commission on Radiological Protection (ICRP) is optimization; specifically, "all radiation exposures should be kept as low as reasonably achievable (ALARA) with economic and social factors taken into account". Prior reviews of circumstances contributing to radiation related injuries revealed that a lack of appreciation by physicians of the magnitude of the skin dose after long exposure times in difficult interventional procedures was a major contributor. Serial digital imaging markedly increases radiation exposure for patients and those undergoing therapeutic procedures are placed at even higher risk.

Despite these dangers, digital subtraction angiography remains the imaging modality of choice for many interventional and endovascular procedures. The use of biplanar DSA provides clinicians with fast, high-quality imaging of the neurovasculature allowing them to more optimally address cranial pathologies endovascularly. The visualization benefits afforded by biplanar DSA comes at the cost of high cumulative radiation dosages. Some studies have reported (http://pubs.rsna.org/doi/full/10.1148/radiol.13121262) baseline dosages for a typical procedure using biplanar DSA around 1.04 Gy. Factors that influence the amount of radiation used include the intended use of DSA for diagnosis or intervention, external monitor settings, collimation, and procedure complexity.

Many approaches exist to reduce the amount of radiation dosages for DSA. Study optimizations such as collimation, patient positioning, radiation dose parameters, and frame-rate settings have significantly reduced overall radiation exposure. Many authors have focused on reducing radiation dosages for DSA by quantifying the effects of these parameters. Balter et al. described a method of frame rate regulation to decrease radiation dose without affecting image quality. By examining system settings on the actual imaging hardware found a 60% reduction, increasable to 75% reduction using noise reduction software (Soderman et al., 2013). Pear et al proved that a variable frame rate and lower pulse rate decreased the radiation dose during cerebral DSA in phantom models. Pyne et al applied a 10 FPS reduction for digital pulse fluoroscopy and cine acquisition. Agarwal et al. introduced low dose techniques to the method of fluoroscopic frame rate reduction. Yi et al reduced radiation dose during fluoroscopy resulting in significantly less radiation exposure, with minimal degradation in imaging quality.

It is well known that the frame rate of the study acquisition directly correlates to cumulative effective dose. In continuous mode, many angiographic devices capture 30 frames per second. It has been shown that a capture of 15 frames per second is sufficient for viewing. Our work focuses on providing clinicians with images at the default, high frame rate using reconstructed images from lower frame rate acquisitions. Adjusting frame-rates, however, limits the amount of information provided by studies, decreasing the resulting images' clinical utility. Our work leverages perfusion modeling to allow for an even greater reduction in frame rate reductions while preserving diagnostic and interventional utility of these images for clinicians by reconstructing high frame-rate images from the underlying models.

Perceived image quality seems to depend on the level of noise. There are two major sources of noise in a radiographic image: quantum noise and background fluctuations. Anatomic structural noise or background fluctuations are formed by overlying anatomy that is not perfectly still throughout the image capture. Noise reduction can be reduced with movement correction (pixel shift) or with the use of temporal filters used to identify and remove information present only on a single image. In our work, we observed high levels of noise when fitting models to all of the available data and that model's fit to lower frame rate studies demonstrated motion resistance due to the nature of the regression. Our simulations demonstrate the potential benefits of using simplified models despite errors introduced by not modeling the residue function.

With perfusion modeling, metrics are highly dependent on the AIF value. Our software calculates perfusion metrics relative to the AT of the AIF voxel found through a local n×n search. Traditionally, there is only one AIF for a provided study. The utility of determining AIF voxels for each voxel allows for the minimization of dispersion effects. Absolute quantification requires knowledge of the concentration of contrast material in the blood pool of interest. This value, called the arterial input function (AIF) is obtained by measuring the artery supplying the area of interest. This software addresses one of the major over-simplifications of perfusion analysis by calculating local AIF for each voxel, performing an n-voxel×n-voxel search at each voxel over the study to identify the voxel with the earliest rise of the tissue concentration curve, and then using that AUC as the CBV for the voxel in question. AIF is a complex function, related to cardiac output, vascular tone, properties of the selected artery, site of contrast injection and partial volume effects related to the small size and volume averaging of intracranial vessels [18], [19]. Measuring perfusion for DSA presents a unique set of problems as each voxel represents a summation of dose response curves. One simplification our model makes is that it assumes a summation of dose response curves are approximated by a single, dominant dose response curve. Accuracy of gamma-variate fits to concentration-time curves from dynamic susceptibility-contrast enhanced MRI has been demonstrated in prior work [9]. In our work, we found that this modeling produces accurate results. The use of quadratic functions tended to over-fit the data and provided less physiologic models.

The major limitations of this study are its relatively small sample size, its single institution nature, the simplifications made during modeling, and its retrospective non-blinded design. The utility of our reader study was that we provided a randomized-control trial evaluating the clinical efficacy of reconstructed images. Other non-modifiable factors affect radiation dose exposure. In their study, Yi et al found that age>60 years had a statistically significant increase in the amount of fluoroscopy and total study time with resultant increases in total radiation dosage. These differences may be attributed to age related factors such as poor vascular access, increased vessel tortuosity, more advanced pathology. Patient diagnoses also affected the amount of radiation received, with findings supporting an increase in the amount of radiation for aneurysms as compared to other vascular pathologies such as occlusion/stenosis or tumor. However, the generality of this approach is capable of reducing the radiation for each patient population.

Software Implementation

FIG. 1 is a block diagram of a software implementation of a system for processing DSA or CT images to reduce radiation exposure to DSA or CT image subjects. Referring to FIG. 1, a computing platform 100 may include a graphics processing unit 102 and a memory 104. A model fitter 106 receives as input captured DSA or CT images. The captured DSA or CT images may be acquired at a reduced frame rate over that conventionally required for a DSA or CT diagnostic imaging study or procedure. In one example, the frame rate for image acquisition can be scaled down by a constant factor (e.g., if standard DSA or CT imaging captures 100 frames for a study, the number of frames can be reduced to 50 frames, 33 frames, 25 frames, or 10 frames with even time separation). In another example, the frame rate for image acquisition can be scaled down by variable factors. For example, instead of increasing the constant time between image captures, image acquisition times can be distributed unevenly based on the phase of contrast agent perfusion so that images acquired at different times are more likely to result in different data points with regard to contrast agent flow. It is desirable to acquire images when contrast agent flow is increasing or decreasing, rather than to acquire multiple images when the flow of contrast agent is constant. In one example, image acquisition may be distributed as follows: instead of 100 frames evenly distributed, 10 frames may be captured during the arterial phase, 50 frames may be captured during the capillary phase, and 10 frames may be captured during the venous phase (the arterial phase may be 3 frames/sec, the capillary phase may be 20 frames/sec, and the venous phase may be 3 frames/sec).

Model fitter 106 fits a model to contrast agent flow across the DSA or CT image frames. In one example, as described above, model fitter 106 may fit a gamma variate model to individual voxel data DSA or CT images. A DSA or CT image reconstructor 108 uses the model to produce reconstructed DSA or CT images. The reconstructed DSA or CT images may be generated by sampling the model at time points where it is desirable to produce reconstructed DSA or CT images.

Figure 2:
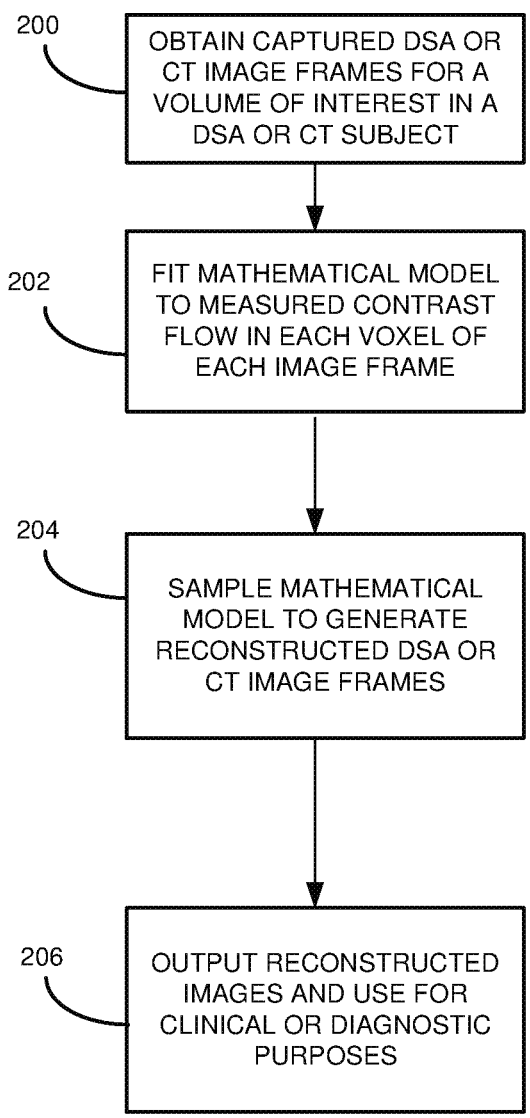
FIG. 2 is a flow chart illustrating an exemplary process for processing DSA or CT images to reduce radiation exposure to DSA or CT subjects.
Figure 3A:
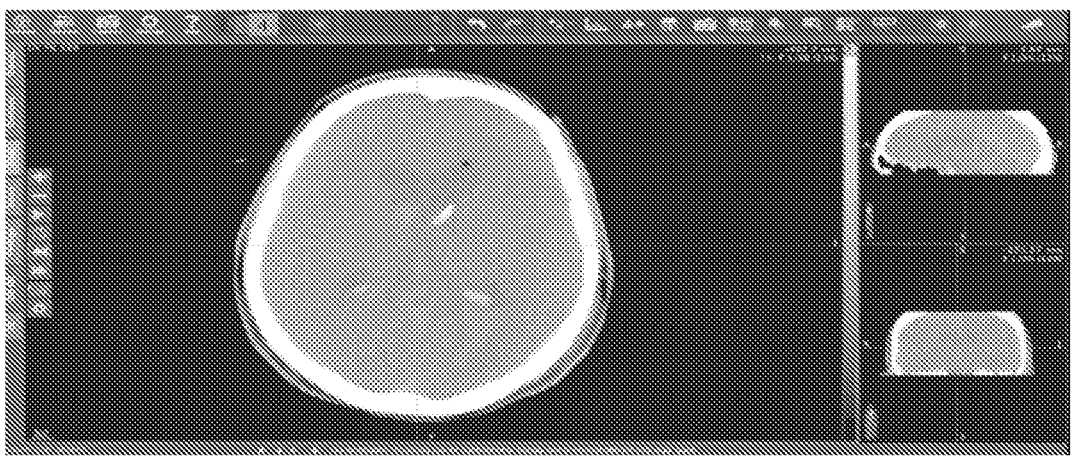
FIGS. 3A-3DD illustrate examples of a series of reconstructed CT images generated using the methodology described herein.
Figure 3B:
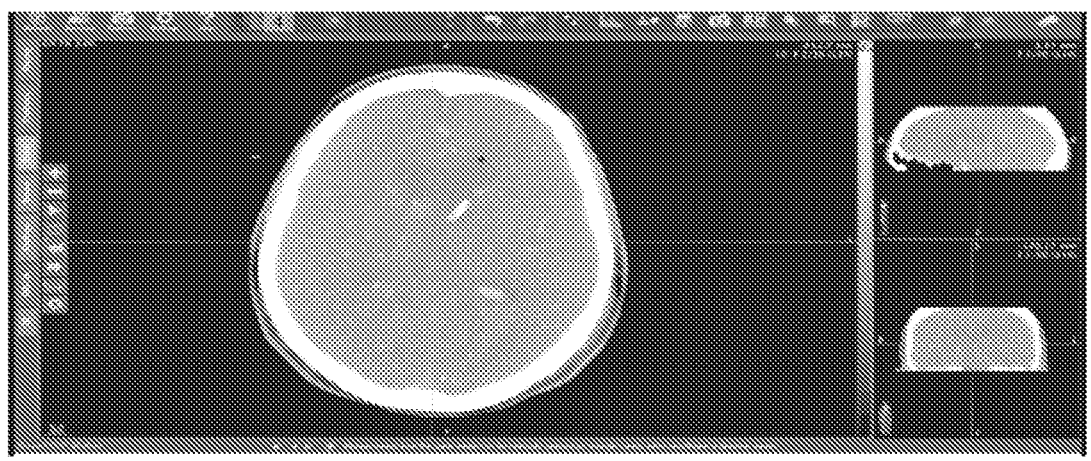
Figure 3C:
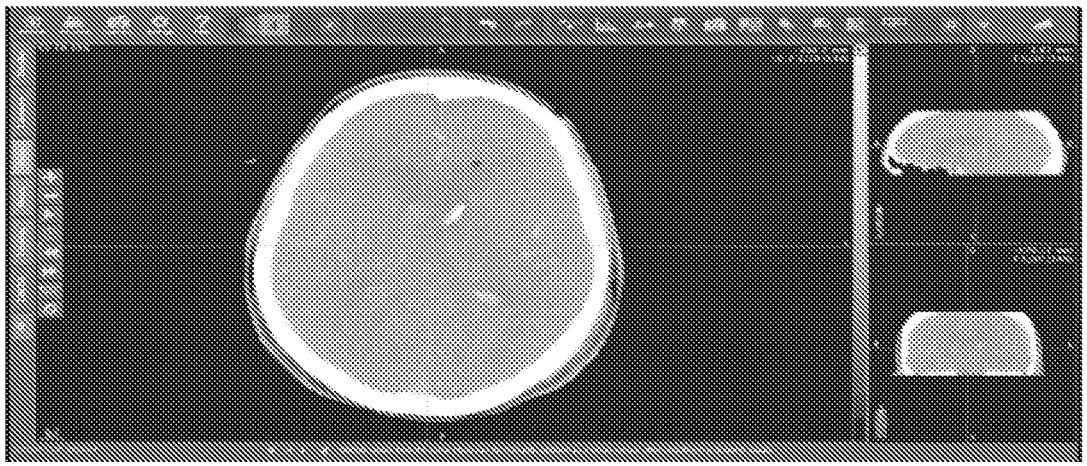
Figure 3D:
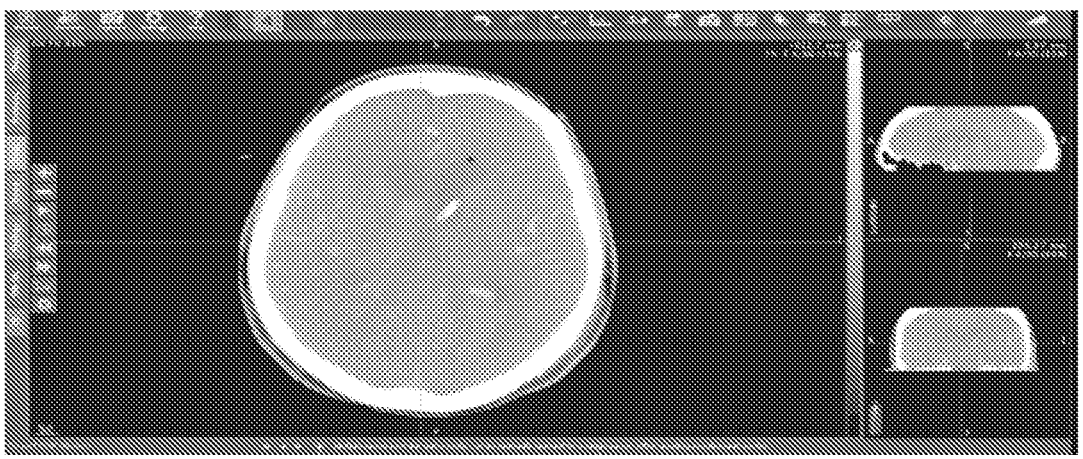
Figure 3E:
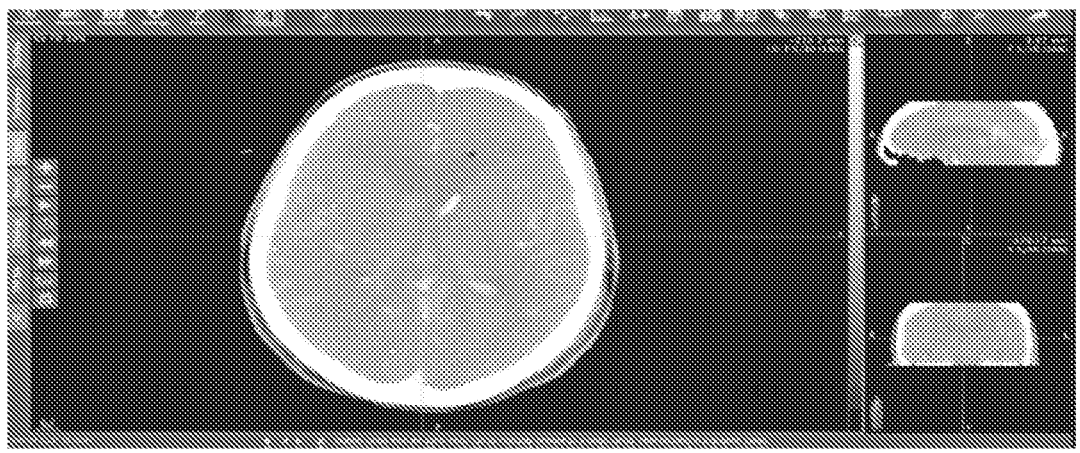
Figure 3F:
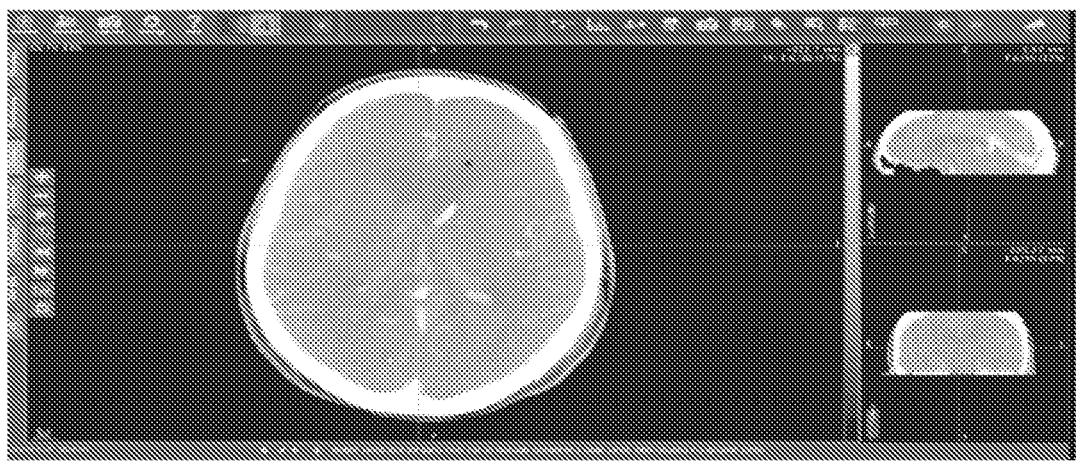
Figure 3G:
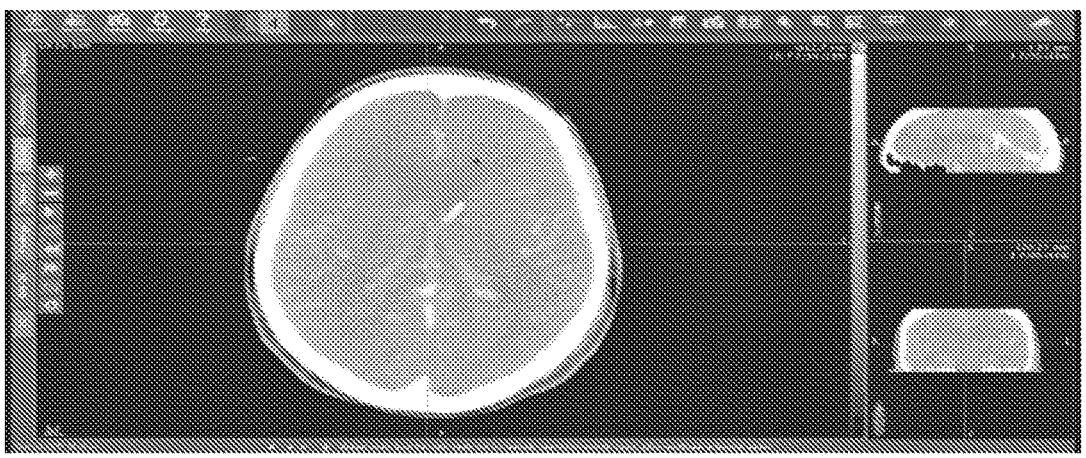
Figure 3H:
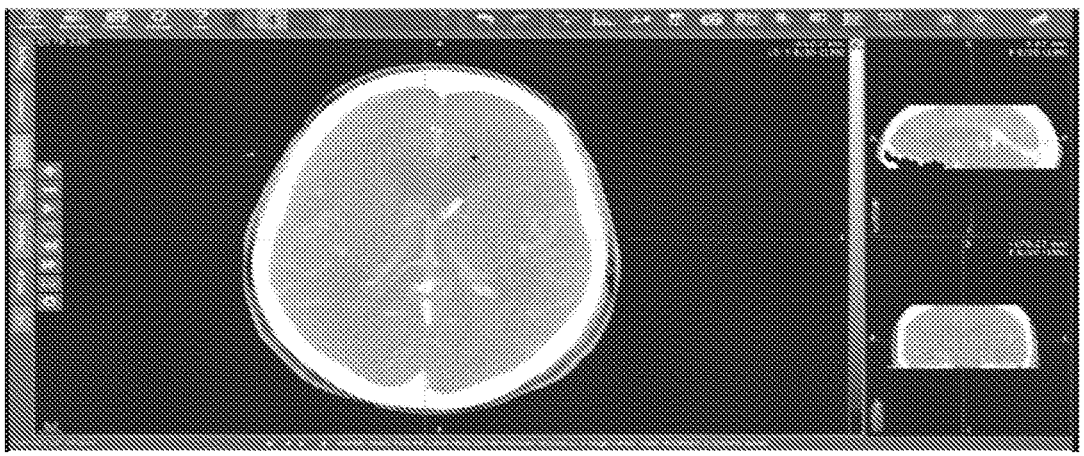
Figure 3I:
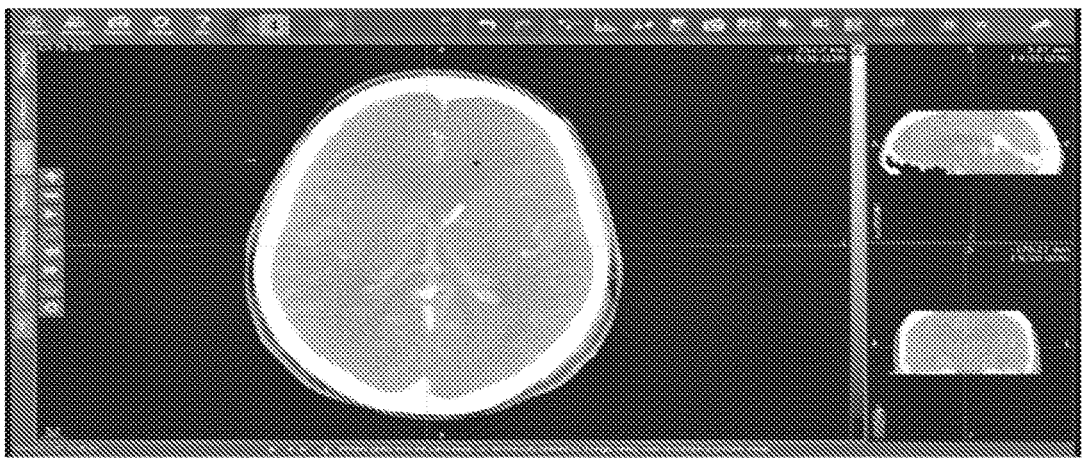
Figure 3J:
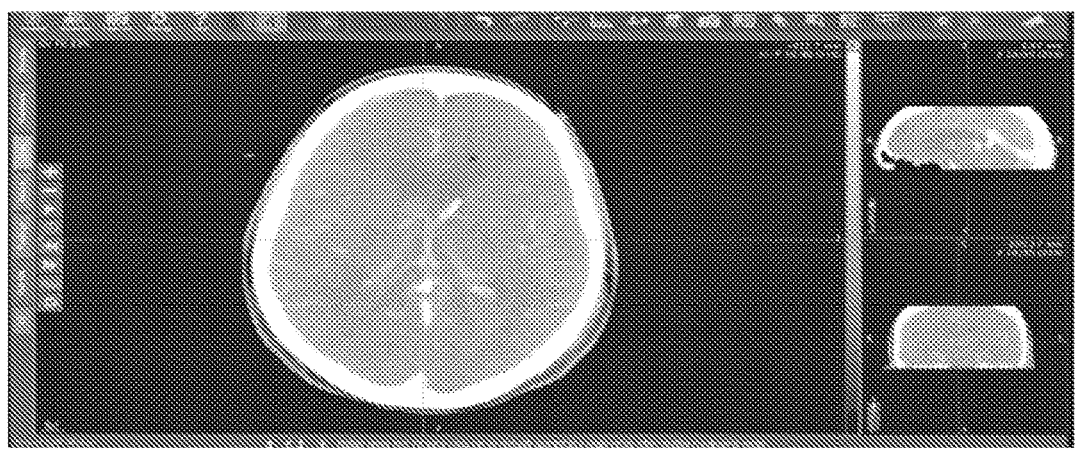
Figure 3K:
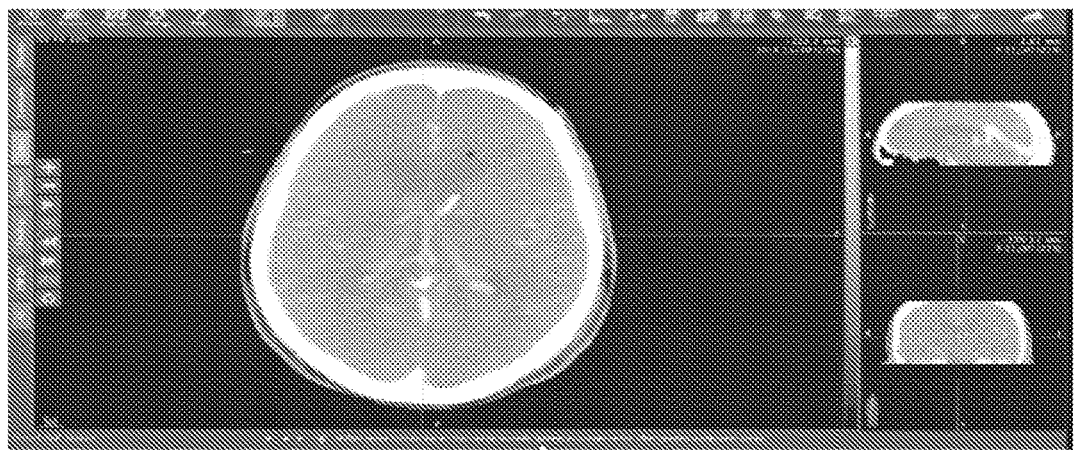
Figure 3L:
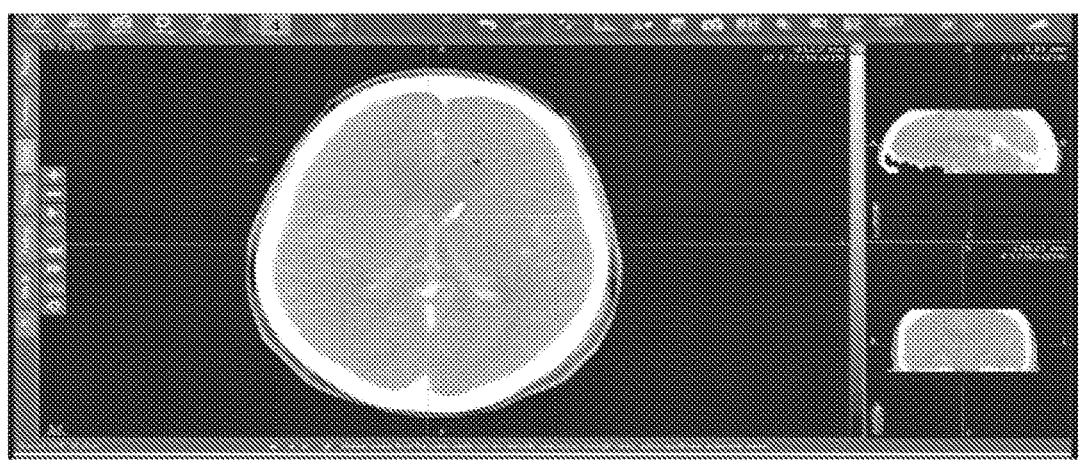
Figure 3M:
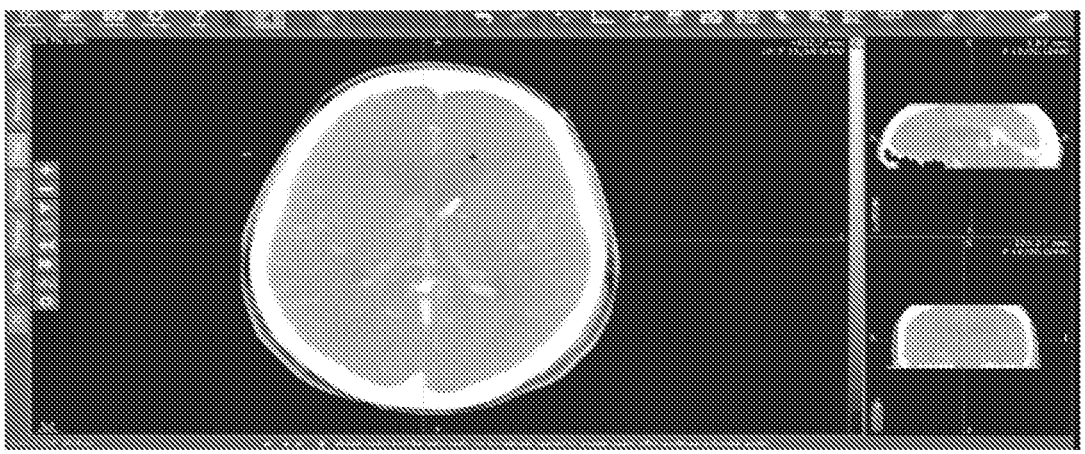
Figure 3N:
Figure 3O:
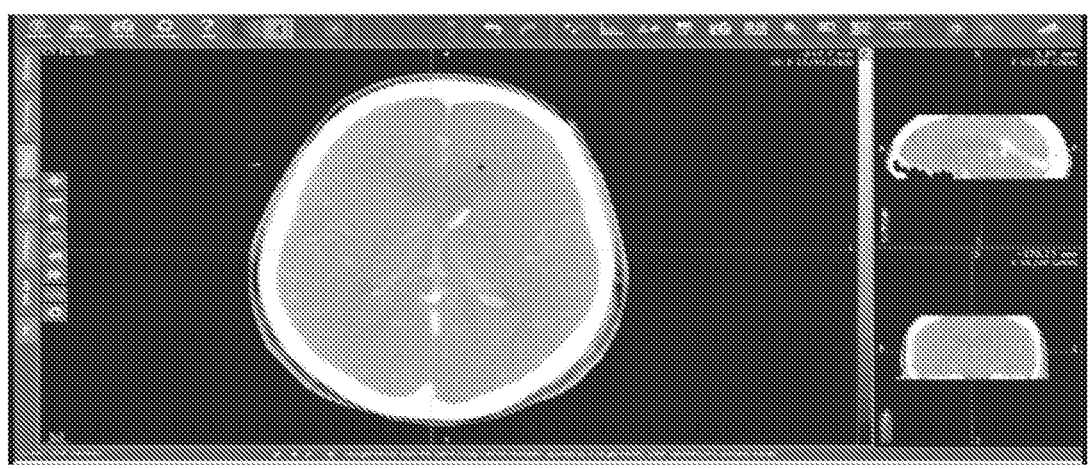
Figure 3P:
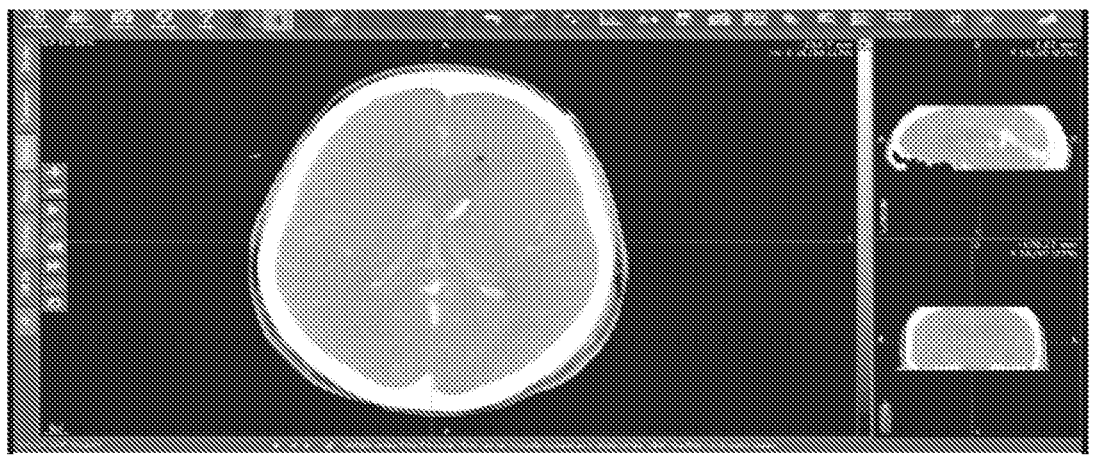
Figure 3Q:
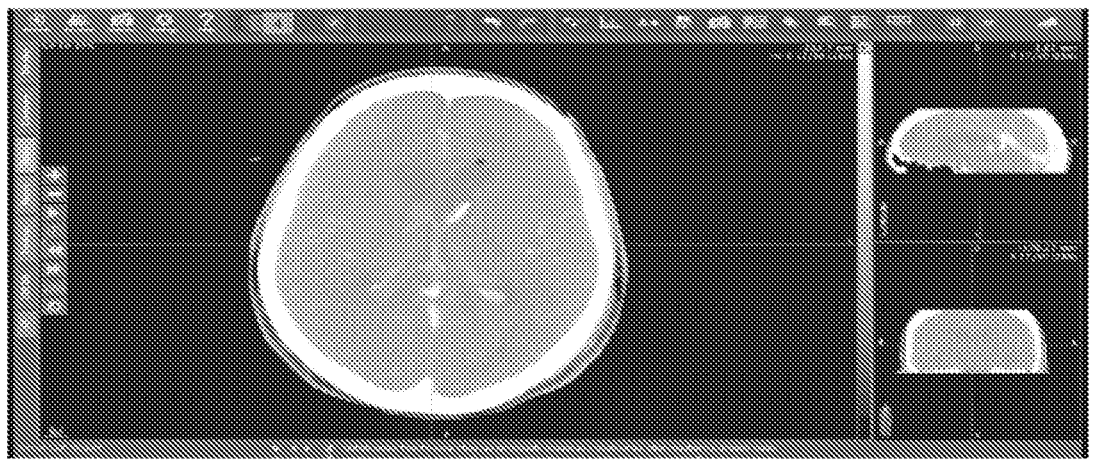
Figure 3R:
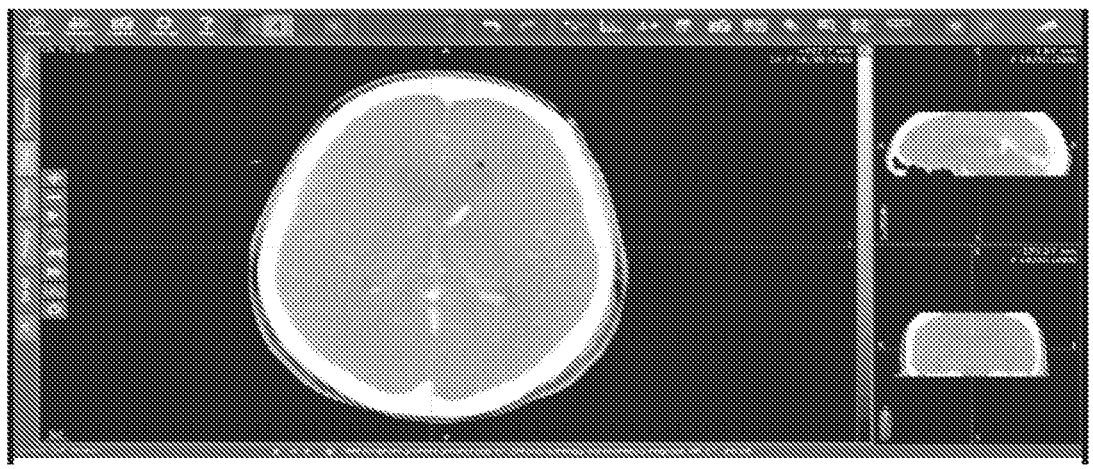
Figure 3S:
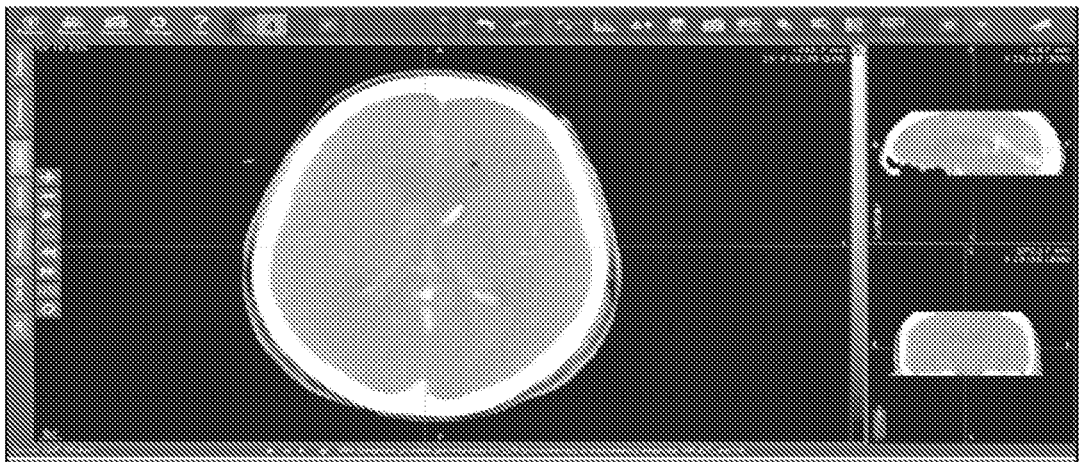
Figure 3T:
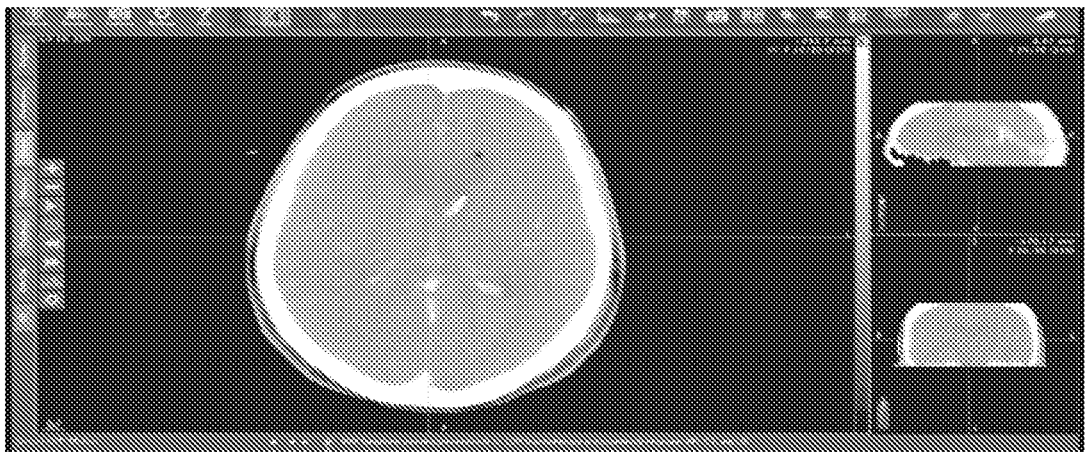
Figure 3U:
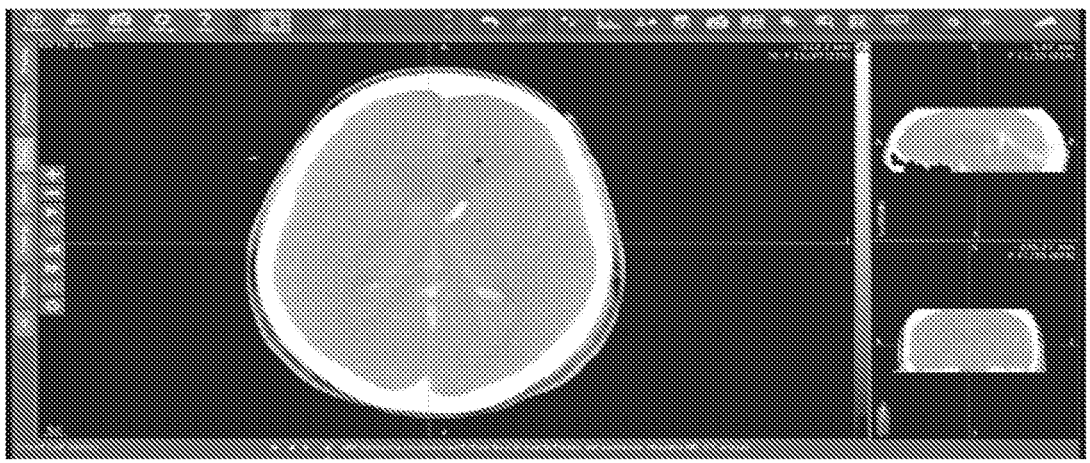
Figure 3V:
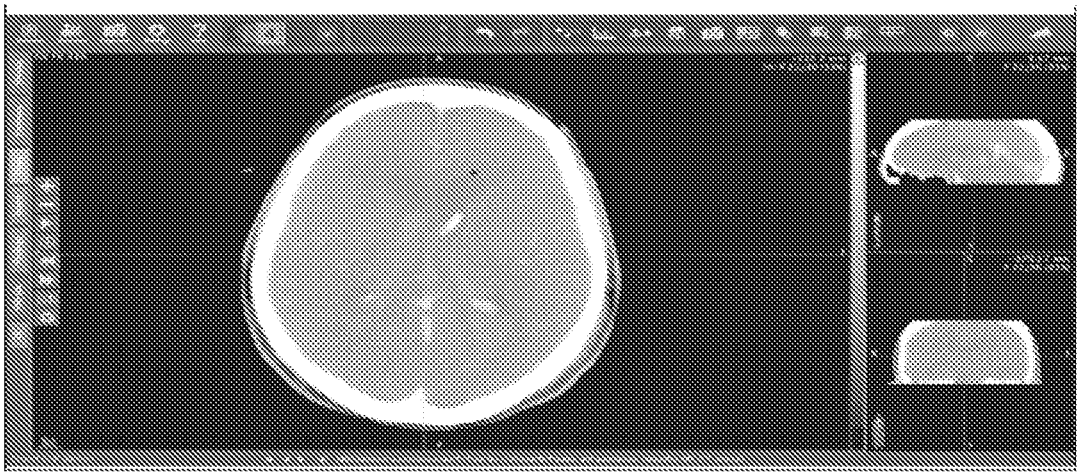
Figure 3W:
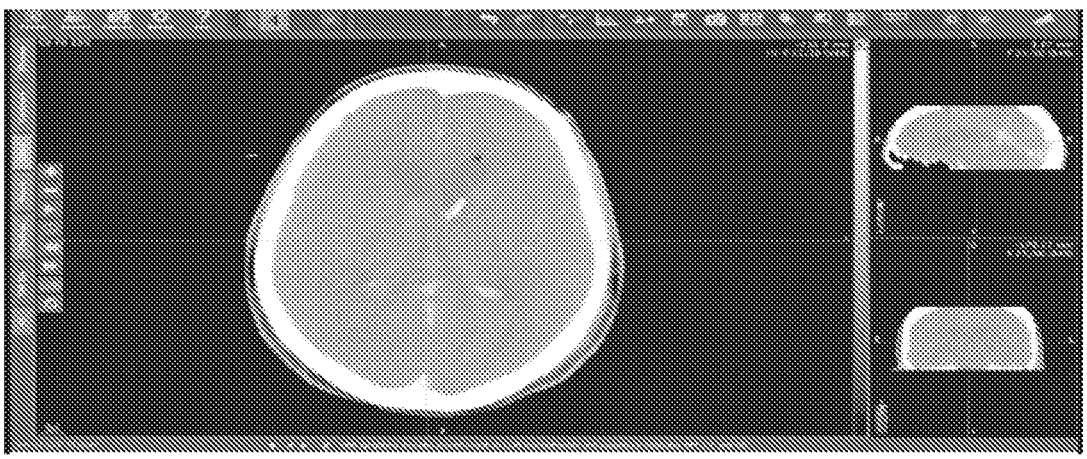
Figure 3X:
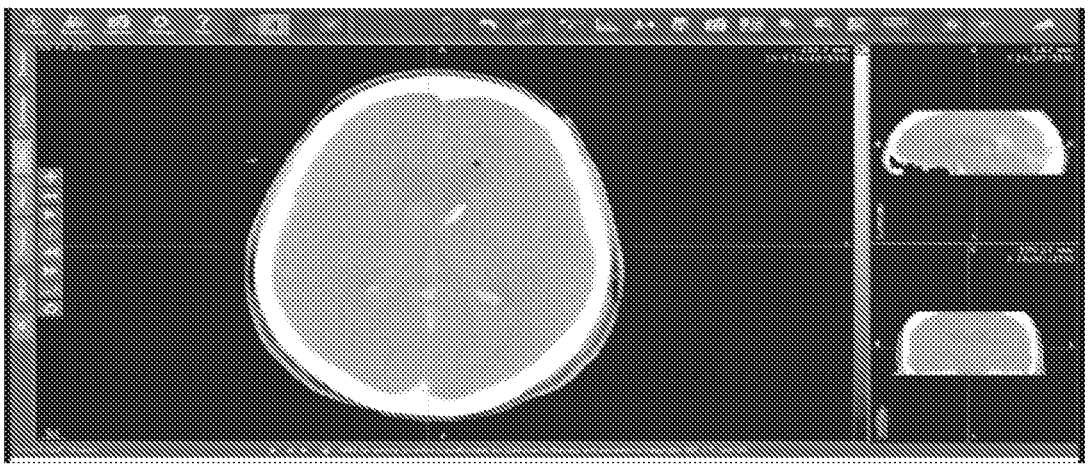
Figure 3Y:
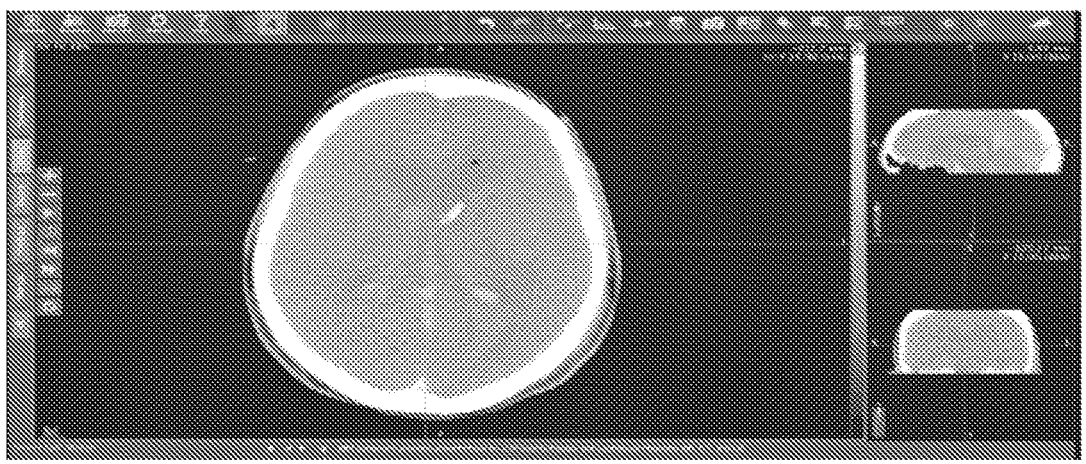
Figure 3Z:
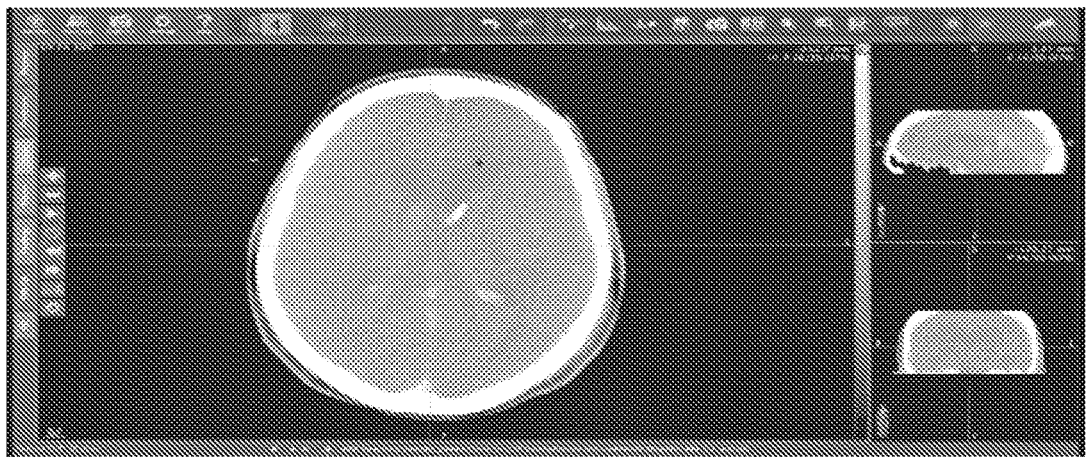
Figure 3A:
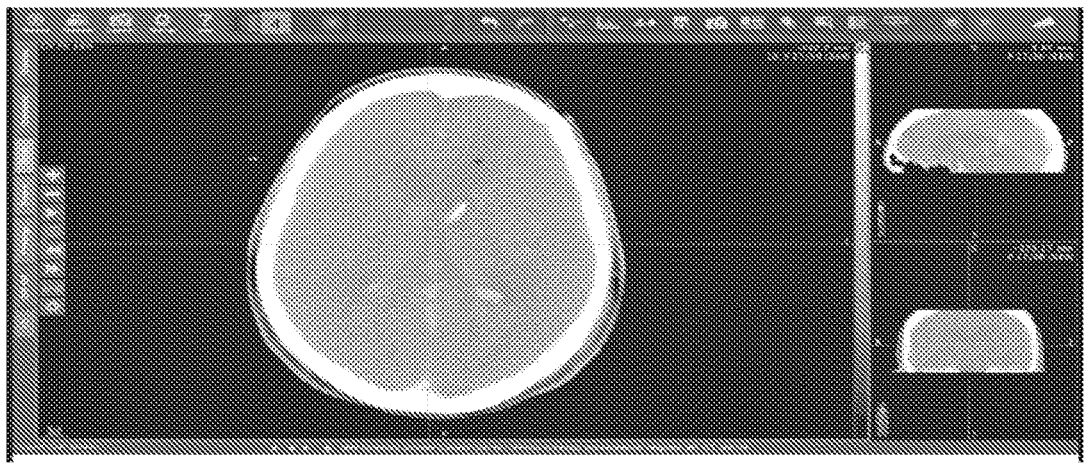
Figure 3B:
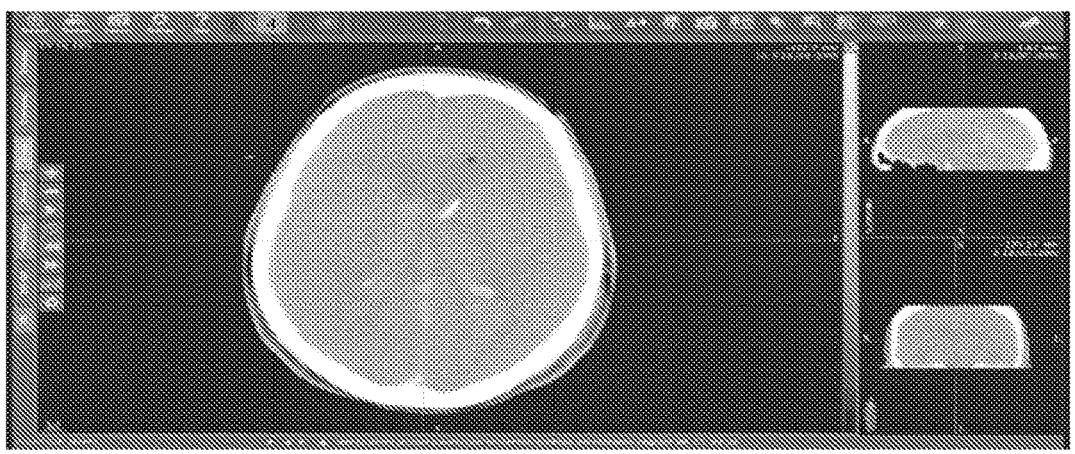
Figure 3C:
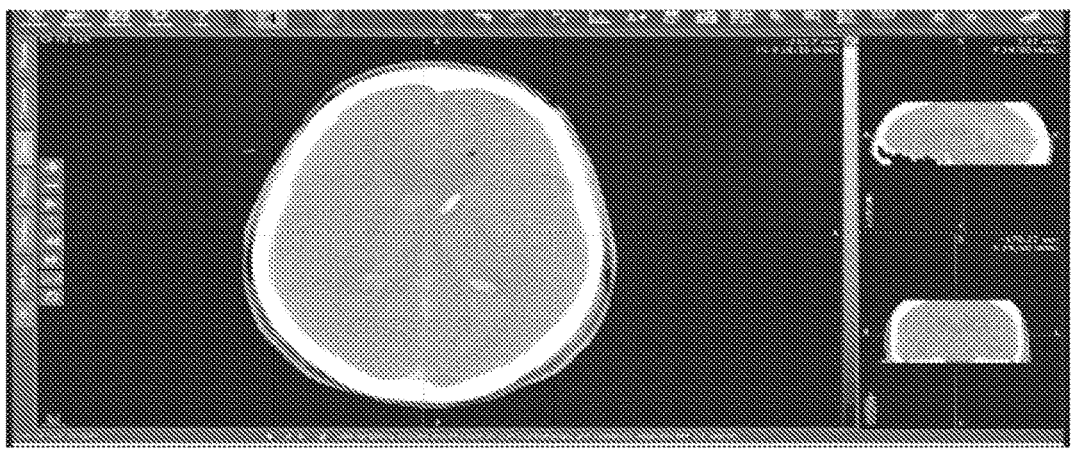
Figure 3D:
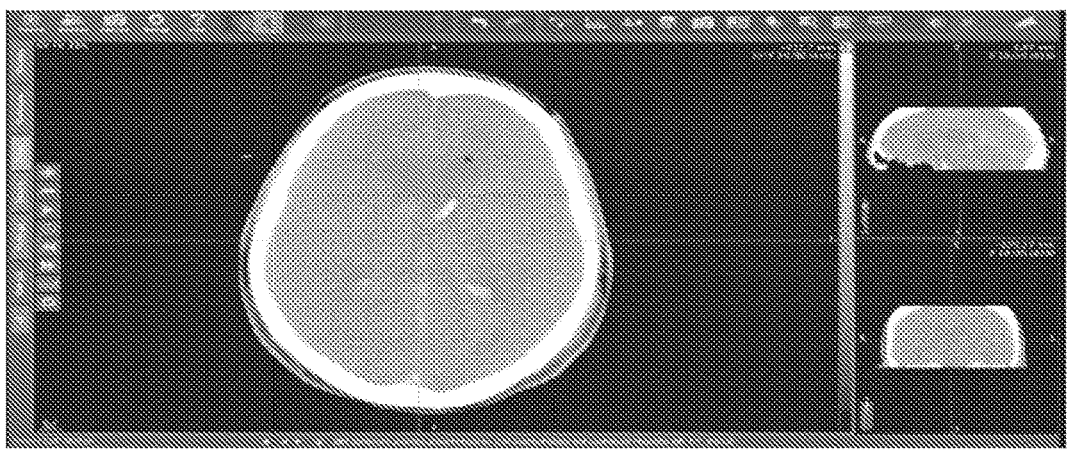
Figure 4A:
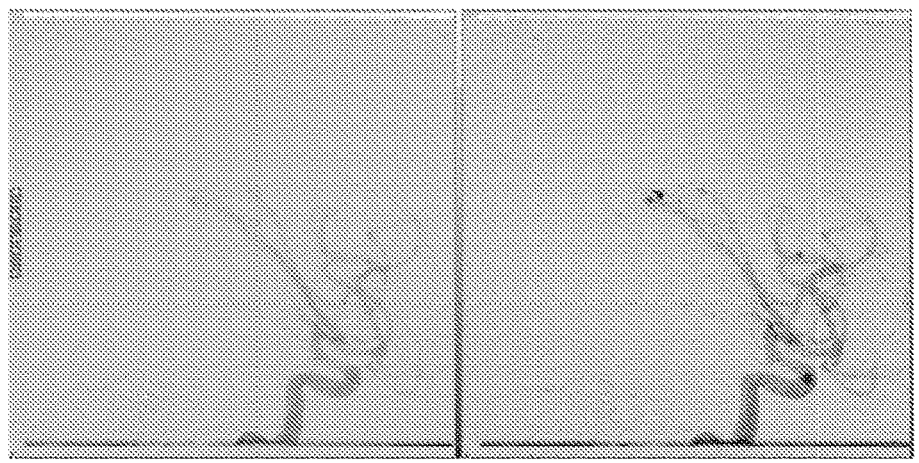
FIGS. 4A-4K are examples of a series of reconstructed DSA images generated using the methodology described herein.
Figure 4B:
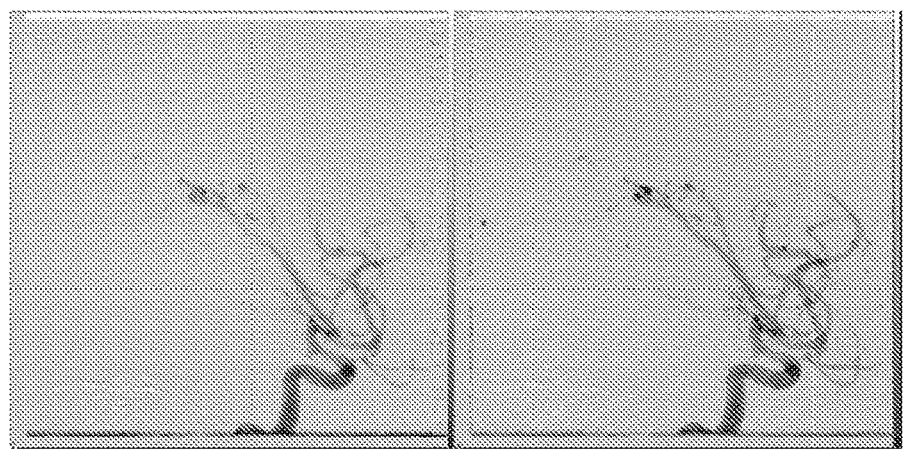
Figure 4C:
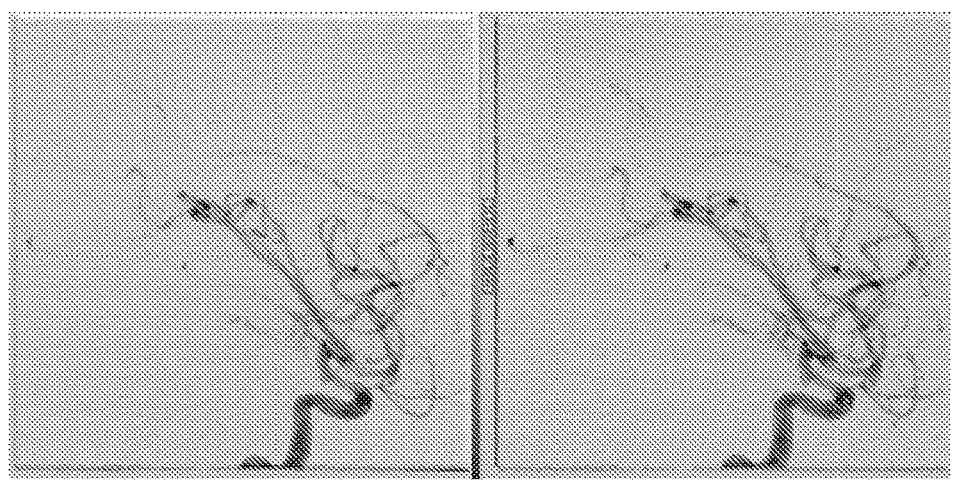
Figure 4D:
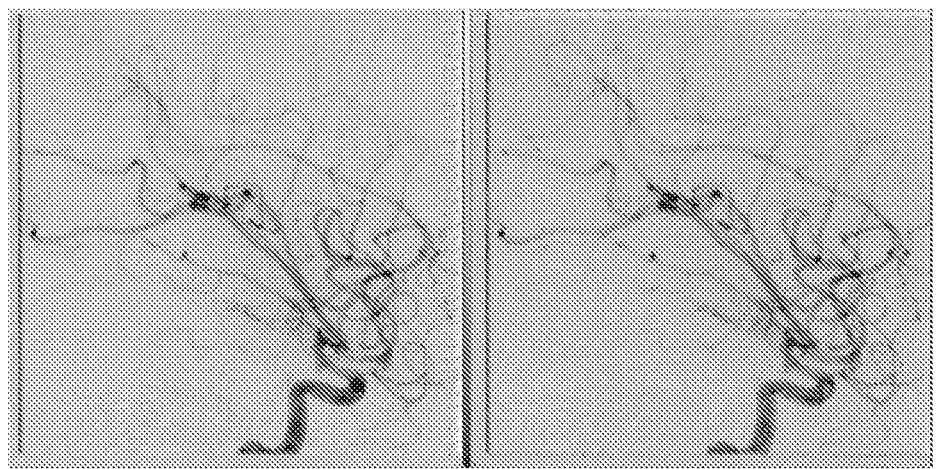
Figure 4E:
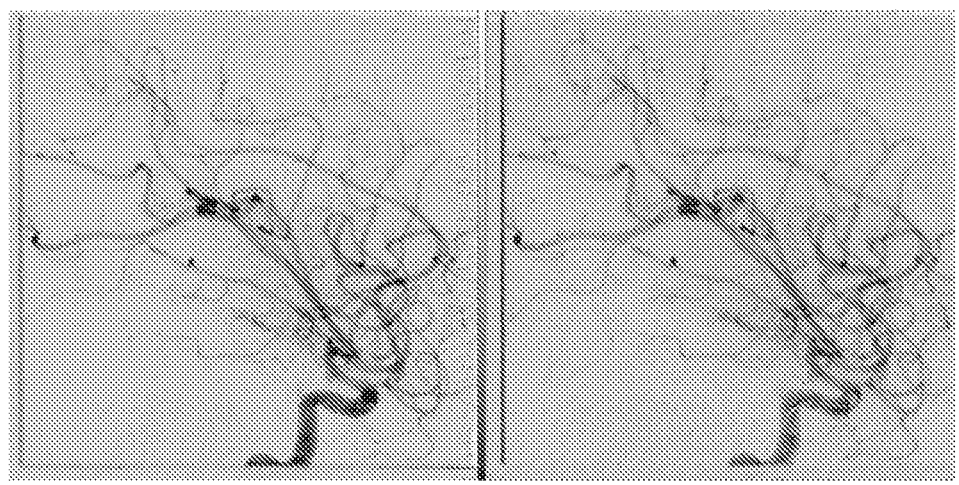
Figure 4F:
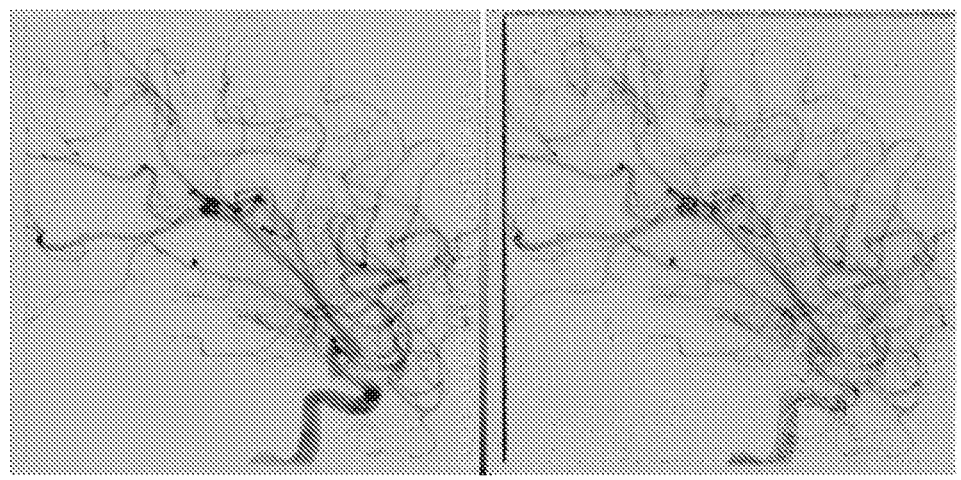
Figure 4G:
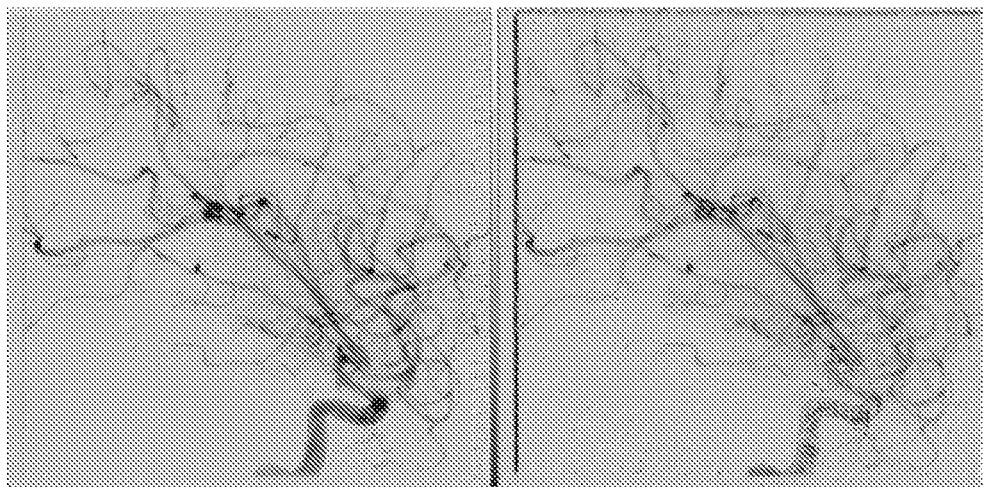
Figure 4H:
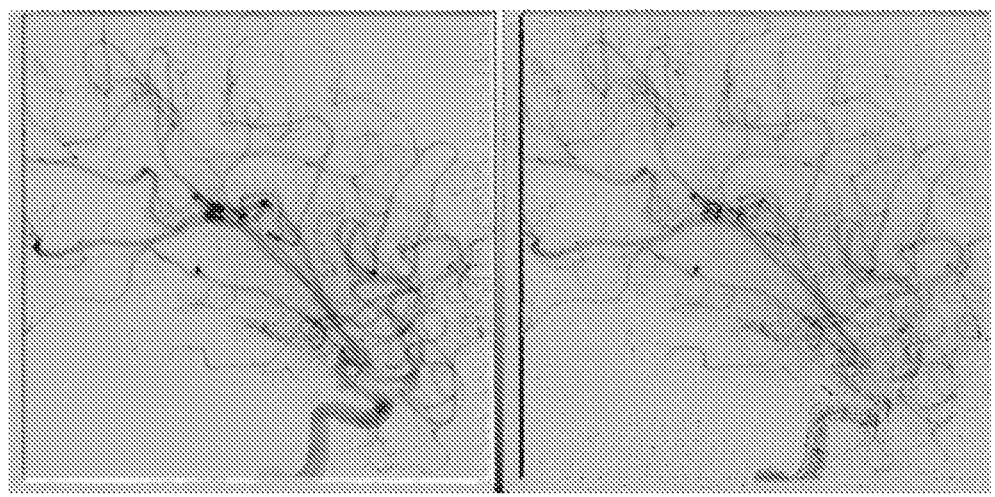
Figure 4I:
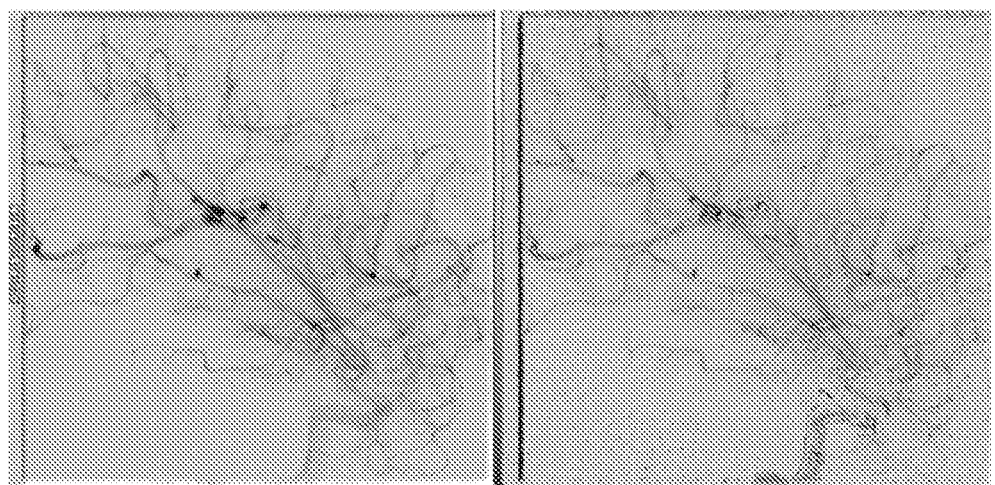
Figure 4J:
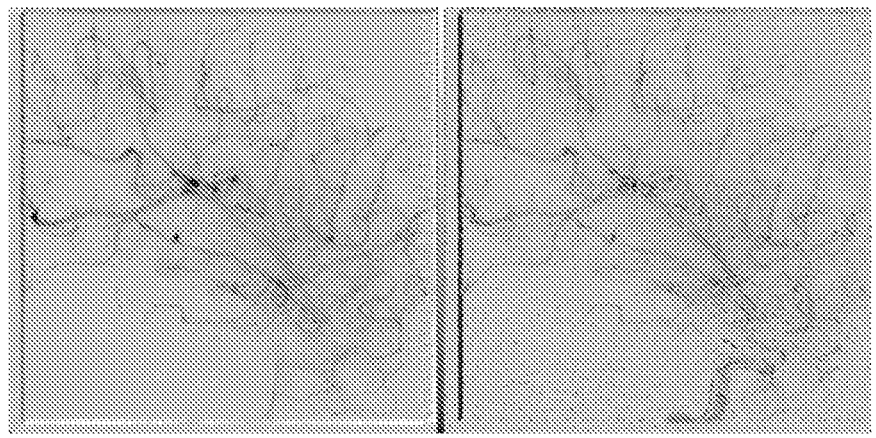
Figure 4K:
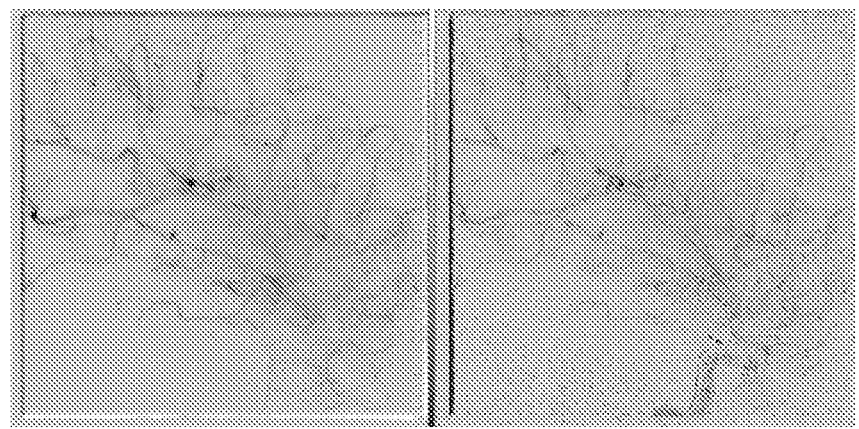

FIG. 2 is a flow chart illustrating an exemplary process for processing CT or DSA images to reduce radiation exposure in DSA or CT subjects. Referring to FIG. 2, in step 200, captured DSA or CT images are obtained for a volume of interest in a DSA or CT subject. For example, the captured images may be obtained at a frame rate that is less than a frame rate normally used for clinical CT or DSA imaging.

In step 202, a mathematical model is a fit to measure contrast flow in each voxel of each image frame. For example, a gamma variate function may be fit to measure contrast agent flow in each voxel in each of the captured image frames.

In step 204, the model is sampled to generate reconstructed DSA or CT image frames. For example, the model may be sampled at time points to generate reconstructed image voxels at time points desired by the user.

In step 206, the reconstructed images may be output and used for a clinical or diagnostic purpose. In one example, the reconstructed images may be output as individual still graphic images. In another example, the reconstructed images may output continuously. FIGS. 3A-3DD and 4A-4K are examples of reconstructed CT and DSA images created using the methodology described herein. More particularly, FIGS. 3A-3DD are examples of a series of reconstructed computed tomography perfusion (CTP) images created using 33% of the original image frames. FIGS. 4A-4K (left images) illustrate original DSA images, and FIGS. 4A-4K (right images) illustrate reconstructed DSA images created using 33% of the original image frames.

The reconstructed images may be used to diagnose any condition for which DSA or CT image is used, such as diagnosis of cerebral blood clots, identification of abnormal arterial branching, etc. The reconstructed images may likewise be used for interventional procedures, such as treatment of clots in blood vessels.

CONCLUSION

Our preliminary work demonstrates DSAs can be performed at a factor of 3 reduction of the radiation dose of current radiation dosages without significant loss of image integrity or resolution and that CT perfusion radiation can be safely reduced by a factor of 10 with minimal loss of definition and diagnostic information. By mathematically modeling dose response curves with this novel approach, we can improve patient safety during imaging with significant reductions in radiation exposure.

The disclosure of each of the following references is hereby incorporated herein by reference in its entirety.

BIBLIOGRAPHY

[1] "Computed Tomography—An Increasing Source of Radiation Exposure—NEJM." [Online]. Available: http://www.nejm.org/doi/full/10.1056/NEJMra072149. [Accessed: 2 Nov. 2017].

[2] R. Krissak et al., "Noise Reduction and Image Quality Improvement of Low Dose and Ultra Low Dose Brain Perfusion CT by HYPR-LR Processing," PLOS ONE, vol. 6, no. 2, p. e17098, February 2011.

[3] F. Austein et al., "Comparison of Perfusion CT Software to Predict the Final Infarct Volume After Thrombectomy," Stroke, vol. 47, no. 9, pp. 2311-2317, September 2016.

[4] J. D. Eastwood, M. H. Lev, and J. M. Provenzale, "Perfusion CT with Iodinated Contrast Material," Am. J. Roentgenol., vol. 180, no. 1, pp. 3-12, January 2003.

[5] L. Lin, A. Bivard, V. Krishnamurthy, C. R. Levi, and M. W. Parsons, "Whole-Brain CT Perfusion to Quantify Acute Ischemic Penumbra and Core," Radiology, vol. 279, no. 3, pp. 876-887, January 2016.

[6] M. Hirata, K. Murase, Y. Sugawara, T. Nanjo, and T. Mochizuki, A method for reducing radiation dose in cerebral CT perfusion study with variable scan schedule, vol. 23. 2005.

[7] S. Niu et al., "Low-dose cerebral perfusion computed tomography image restoration via low-rank and total variation regularizations," Neurocomputing, vol. 197, p. 143, July 2016.

[8] B. E. McGehee, J. M. Pollock, and J. A. Maldjian, "Brain perfusion imaging: How does it work and what should I use?" J. Magn. Reson. Imaging, vol. 36, no.6, pp. 1257-1272, December 2012.

[9] T. Benner, S. Heiland, G. Erb, M. Forsting, and K. Sartor, "Accuracy of gamma-variate fits to concentration-time curves from dynamic susceptibility-contrast enhanced MRI: Influence of time resolution, maximal signal drop and signal-to-noise," Magn. Reson. Imaging, vol. 15, no. 3, pp. 307-317, January 1997.

[10] M. T. Madsen, "A simplified formulation of the gamma variate function-IOPscience." Available:http://iopscience.iop.org.libproxy.lib.unc.edu/article/10 0.1088/0031-9155/37/7/010/metajsessionid=180C0DE85FCCE-B26A3A99 7000382511F.c1.iopscience.cld.iop.org. [Accessed: 2 Nov. 2017].

[11] A. A. Chan and S. J. Nelson, "Simplified gamma-variate fitting of perfusion curves," in 2004 2nd IEEE International Symposium on Biomedical Imaging: Nano to Macro (IEEE Cat No. 04EX821), 2004, p. 1067-1070 Vol. 2.

[12] X. Li, J. Tian, and R. K. Millard, "Erroneous and inappropriate use of gamma fits to tracer-dilution curves in magnetic resonance imaging and nuclear medicine11Re: Benner, et al., 1997. Accuracy of y-variate fits to concentration-time curves from dynamic susceptibility-contrast enhanced MRI: influence of time resolution, maximal signal drop and signal-to-noise. Magn Reson Imag 1997; 15:307-317." Magn. Reson. Imaging, vol. 21, no. 9, pp. 1095-1096, November 2003.

[13] V. Patil and G. Johnson, "An improved model for describing the contrast bolus in perfusion MRI," Med. Phys., vol. 38, no. 12, pp. 6380-6383, December 2011.

[14] J. W. Belliveau et al., "Functional cerebral imaging by susceptibility-contrast NMR," Magn. Reson. Med., vol. 14, no. 3, pp. 538-546, June 1990.

[15] B. R. Rosen, J. W. Belliveau, J. M. Vevea, and T. J. Brady, "Perfusion imaging with NMR contrast agents," Magn. Reson. Med., vol. 14, no. 2, pp. 249-265, May 1990.

[16] B. R. Rosen et al., "Contrast agents and cerebral hemodynamics," Magn. Reson. Med., vol. 19, no. 2, pp. 285-292, June 1991.

[17] M. Koenig, E. Klotz, B. Luka, D. J. Venderink, J. F. Spittler, and L. Heuser, "Perfusion CT of the brain: diagnostic approach for early detection of ischemic stroke.," Radiology, vol. 209, no. 1, pp. 85-93, October 1998.

[18] A. Jackson, "Analysis of dynamic contrast enhanced MRI," Br. J. Radiol., vol. 77, no. suppl_2, pp. S154-S166, December 2004.

[19] M. J. Paldino and D. P. Barboriak, "Fundamentals of Quantitative Dynamic Contrast-Enhanced MR Imaging," Magn. Reson. Imaging Clin., vol. 17, no. 2, pp. 277-289, May 2009.

[20] J. Bredno, M. E. Olszewski, and M. Wintermark, "Simulation model for contrast agent dynamics in brain perfusion scans," Magn. Reson. Med., vol. 64, no. 1, pp. 280-290, July 2010.

[21] Chan, Antoinette A., and Sarah J. Nelson. "Simplified gamma-variate fitting of perfusion curves." Biomedical Imaging: Nano to Macro, 2004. IEEE International Symposium on. IEEE, 2004.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for processing digital subtraction angiography (DSA) or computed tomography (CT) images for reduced radiation exposure to a DSA or CT subject, the method comprising:
   receiving, as input, a plurality of captured DSA or CT image frames of a contrast agent flowing through a volume of interest in a subject;
   fitting a mathematical model to measured contrast agent density of individual voxels of the captured DSA or CT image frames to produce a mathematical model of contrast agent flow across the captured DSA or CT image frames;
   sampling the mathematical model of contrast agent flow for the individual voxels to produce reconstructed DSA or CT image frames; and
   outputting at least one of the reconstructed CT or DSA image frames.

2. The method of claim 1 wherein the mathematical model comprises a gamma variates model.

3. The method of claim 1 wherein the mathematical model comprises a $4^{th}$ order polynomial model.

4. The method of claim 1 wherein obtaining a plurality of captured DSA or CT image frames includes obtaining N captured DSA or CT image frames, where N is an integer less than a number of DSA or CT image frames used in a clinical application of DSA or CT image frames without using image reconstruction.

5. The method of claim 4 wherein the N captured DSA or CT images are acquired with an even time separation between image acquisition times.

6. The method of claim 4 wherein the N captured DSA or CT images are acquired with at least some uneven time separations between image acquisition times.

7. The method of claim 6 wherein the at least some uneven time separations are structured to acquire images at different frame rates during arterial, capillary, and venous phases of contrast agent perfusion.

8. The method of claim 1 wherein the DSA or CT image frames comprise DSA image frames.

9. The method of claim 1 wherein the DSA or CT image frames comprise CT image frames.

10. A system for processing digital subtraction angiography (DSA) or computed tomography (CT) images for reduced radiation exposure to a DSA or CT subject, the system comprising:
  a computing platform including at least one processor;
  a model fitter executable by the at least one processor for receiving, as input, a plurality of captured DSA or CT image frames of a contrast agent flowing through a volume of interest in a subject and fitting a mathematical model to measured contrast agent density of individual voxels of the captured DSA or CT image frames to produce a mathematical model of contrast agent flow across the captured DSA or CT image frames; and
  an image reconstructor executable by the at least one processor for sampling the mathematical model of contrast agent flow for the individual voxels to produce reconstructed DSA or CT image frames and outputting at least one of the reconstructed CT or DSA image frames.

11. The system of claim 10 wherein the mathematical model comprises a gamma variates model.

12. The system of claim 10 wherein the mathematical model comprises a $4^{th}$ order polynomial model.

13. The system of claim 10 wherein obtaining a plurality of captured DSA or CT image frames includes obtaining N captured DSA or CT image frames, where N is an integer less than a number of DSA or CT image frames used in a clinical application of DSA or CT image frames without using image reconstruction.

14. The system of claim 13 wherein the N captured DSA or CT images are acquired with an even time separation between image acquisition times.

15. The system of claim 13 wherein the N captured DSA or CT images are acquired with at least some uneven time separations between image acquisition times.

16. The system of claim 15 wherein the at least some uneven time separations are structured to acquire images at different frame rates during arterial, capillary, and venous phases of contrast agent perfusion.

17. The system of claim 10 wherein the DSA or CT image frames comprise DSA image frames.

18. The system of claim 10 wherein the DSA or CT image frames comprise CT image frames.

19. A non-transitory computer readable medium having stored thereon executable instructions that when executed by a processor of a computer control the computer to perform steps comprising:
  receiving, as input, a plurality of captured DSA or CT image frames of a contrast agent flowing through a volume of interest in a subject;
  fitting a mathematical model to measured contrast agent density of individual voxels of the captured DSA or CT image frames to produce a mathematical model of contrast agent flow across the captured DSA or CT image frames;
  sampling the mathematical model of contrast agent flow for the individual voxels to produce reconstructed DSA or CT image frames; and
  outputting at least one of the reconstructed CT or DSA image frames.

* * * * *